United States Patent [19]
Strom et al.

[11] Patent Number: 5,958,403
[45] Date of Patent: Sep. 28, 1999

[54] METHODS AND COMPOUNDS FOR PREVENTION OF GRAFT REJECTION

[75] Inventors: Terry Strom, Brookline; Towia Libermann, Newton, both of Mass.

[73] Assignee: Beth Israel Hospital Association, Boston, Mass.

[21] Appl. No.: 08/273,402

[22] Filed: Jul. 11, 1994

Related U.S. Application Data

[63] Continuation-in-part of application No. 08/024,569, Mar. 1, 1993, abandoned, which is a continuation-in-part of application No. 07/843,731, Feb. 28, 1992, abandoned.

[51] Int. Cl.$^6$ .............................. C12N 15/63; A61K 48/00
[52] U.S. Cl. .......................................... 424/93.21; 514/44
[58] Field of Search ............................. 514/44; 424/93.21

[56] References Cited

U.S. PATENT DOCUMENTS

| 4,675,285 | 6/1987 | Clark et al. |
| 5,171,841 | 12/1992 | Laurence |

OTHER PUBLICATIONS

Aruffo, A., et al., Molecular cloning of a CD28 CDNA by a high-efficiency COS cell expression system, PNAS 84:8573–7, 1987.
Blackman, M.A., et al., A role for clonal inactivation in T–cell tolerance to Mls–1a, Nature 345:540, 1990.
Boitard, C., et al., T–cell–mediated inhibition of the transfer of autoimmune diabetes in NOD mice, J. Exp. Med. 169:1669, 1989.
Bottazzo, G.F., et al., In situ characterization of autoimmune phenomena and expression of HLA molecules in the pancreas in diabetic insulitis, N. Eng. J. Med. 313:353, 1985.
Burkly, L.C., et al., T–cell tolerance by clonal energy in transgenic mice with nonlymphoid expression of MHC class II I–E, Nature 342:564, 1989.
Burkly, L.C., et al., Tolerance in transgenic mice expressing major histocompatibility molecules extrathymically on pancreatic cells, Science 248:1364, 1990.
Charlton, B., et al., Cyclophosphamide–induced diabetes in NOD/WEHI mice. Evidence for suppression in spontaneous autoimmune diabetes mellitus, Diabetologia 38:441, 1989.
Chiu, C–P., et al., Multiple biological activities are expressed by a mouse interleukin 6 cDNA clone isolated from bone marrow stromal cells, PNAS 85:7099, 1988.
Danielpour, D., et al., Immunodetection and quantitation of the two forms of transforming growth factor–beta (TGF–beta 1 and TGF–beta 2) secreted by cells in culture, J. Cel. Physiol. 138:79, 1989.
Derynck, R., et al., The murine transforming growth factor–β precursor, J. Biol. Chem. 261:4377, 1986.
Fink, P.J., et al., Veto cells, Ann. Rev. Imunol. 6:115, 1988.
Fransen, L., et al., Molecular cloning of mouse tumor necrosis factor cDNA and its eukaryotic expression, Nucl. Ac. Res. 13:4417, 1985.
Gillis, S., et al., Long term culture of tumour specific cytotoxic T–cells, Nature 268:154, 1977.

Gray, P.W., et al., Cloning and expression of murine immune interferon cDNA, PNAS 80:5842, 1983.
Kaplan, G., et al., Rational immunotherapy with interleukin 2, Bio/Tech. 10:157–62, 1982.
Bromberg, Current Opinion in Immunology, 7:639–643, 1995.
Morris, Cell Transplantation, 2:7–12, 1993.
Chavin et al., Surgical Forum, 44(0):407–409, 1993.
Tahara et al., Transplantation Proceedings, 24(6):2975–2976, Dec. 1992.
Libermann et al., J. American Society of Nephrology, 6(3):1059, abstract 333, Sep. 1995.
Spits et al., Int. Arch. Allergy Immunol., 99:8–15, 1992.
Antin et al., Blood, 80(12):2964–2968, Dec. 15, 1992.
Diaz–Gallo et al., J. American Society of Nephrology, 3(3):583, abstract 82P, Sep. 1992.
Kelley et al., Blood Purification, 13:199–205, 1995.
Ricordi et al., Clinical Transplantation, 7:75–81, 1993.
Broadley et al., FASEB J., 5(4):A539, 1991.
Kappler, J.W., et al., T–cell tolerance by clonal elimination in the thymus, Cell 49:273, 1987.
Kashima, N., et al., Unique structure of murine interleukin–2 as deduced from cloned cDNAs, Nature 313:402, 1985.
Lee, F., et al., Isolation and characterization of a mouse interleukin cDNA clone that expresses B–cell stimulatory factor 1 activities and T–cell–and mast–cell–stimulating activities, PNAS 83:2061, 1986.
Makino, S. et al., Breeding of a non–obese, diabetic strain of mice, Exp. Anim. 29:1, 1980.
Miyazaki, A., et al., Predominance of T Lymphocytes in pancreatic islets of spleen of pre–diabetic non–obese diabetic (NOD) mice: a longitudinal study, Clin. Exp. Immunol. 60:622, 1985.
Mueller, D.L., et al., Clonal expansion versus functional clonal inactivation. A costimulatory signalling pathway determines the outcome of T–cell antigen receptor occupancy, Ann. Rev. Immunol 7:445, 1989.
Murray, L.J., et al., In vivo cytokine gene expression in T–cell subsets of the autoimmune MRL/MP–lpr/lpr mouse, Eur. J. Immunol. 20:163, 1990.

(List continued on next page.)

*Primary Examiner*—Brian R. Stanton
*Assistant Examiner*—Karen M. Hauda
*Attorney, Agent, or Firm*—Fish & Richardson P.C.

[57] ABSTRACT

Disclosed is a method of localized immunosuppression which may be used for preventing graft rejection or for preventing tissue destruction due to autoimmune disease. Also disclosed is a protein suppressor factor that is secreted by cloned anergic T-cells, blocks interleukin 2 (IL-2) stimulated T-cell proliferation, has an apparent molecular weight of between 10 and 30 kilodaltons, can be inactivated by heating to 65° C. for 15 minute, blocks interleukin 4 (IL-4) stimulated T-cell proliferation in vitro, is non-cytotoxic to T-cells, and does not inhibit the production of IL-2 by T-cells in vitro.

1 Claim, 16 Drawing Sheets

OTHER PUBLICATIONS

Ortaldo, J.R., et al., Mechanistic studies of transforming growth factor–B inhibition of IL–2 dependent activation of CD3–large granular lymphocyte functions, J. Immunol. 146:3791, 1991.

Pankewycz, O., et al., Islet–infiltrating T–cell clones from non–obese diabetic mice that promote or prevent accelerated onset of diabetes, Eur. J. Immunol. 21:873, 1991.

Ruegemer, J.J., et al., Regulatory effects of transforming growth factor–B on IL–2 and IL–4 dependent cell cycle progression, J. Immunol. 144:1767, 1990.

Russell, J.H., et al., Receptor–stimulated death pathway is opened by antigen in mature T–cells, Proc. Natl. Acad. Sci. USA 88:2151, 1991.

Webb, S., et al., Extrathymic tolerance of mature T–cells: Clonal elimination as a consequence of immunity Cell, 63:1249, 1990.

Wicker, L.S., et al., Transfer of autoimmune diabetes mellitus with splenocytes from nonobese diabetic (NOD) mice, Diabetes 35:855, 1986.

Schwyzer et al., Partial Purification and Biochemical Characterization of AT Cell Suppressor Factor Produced by Human Glioblastoma Cells, J. Immun. 134(2):1003–1009, 1985.

Kuppner et al., The Glioblastoma–Derived T–Cell Suppressor Factor/Transforming Growth Factor Beta$_2$ Inhibits the Generation of Lymphokine–Activated Killer (LAK) Cells, Int. J. Cancer 42:562–567 1988.

Colizzi et al., Suppressor cells induced by BCG release non–specific factors in vitro which inhibit DNA DNA synthesis and interleukin–2 production, J. Immun. 51:65–71, 1984.

Almawi et al., Induction of Suppression by a Murine Non-specific Suppressor–Inducer Cell Line (M1–A5). III. Partial Purification of the Suppressor Cell–Inducing Factors, J. Mol. Cell Immunol. 3:156–166, 1987.

Redondo et al., Inhibition of interleukin 2–induced proliferation of cloned murine T cells by Glucocorticoids Possible involvement of an inhibitory protein, Eur. J. Immunol. 18:1555–1559, 1988.

Fidel et al., Regulation of Granulomatous Inflammation in Murine Schistosomiasis, J. of Immunol. 146:1941–1948, 1991.

Mosman, Current Protocols in Immunology, 1:6.14.1–6.14.8, 1991.

Gotoh et al., "Brief Communications", Transplantation 40:437–438.

Fiorentino et al., "IL–10 Inhibits Cytokine Production by Activated Macroophages", The American Association of Immunologists, 147(11):3815–3822, 1991.

Bloom, J. Clinical Investigation 91:1265–1266, 1993.

Diat–Gallo, PNAS 89:8566–8660, 1991.

Business Newsweek, Issued May 28, 1990, "The Genetic Age", pp. 68–83.

AP-1/NF-IL6/NF-κB/C ILA4-Ig/pxf3 nahR/c-fos/CTLA4-Ig/pxf3

IL-6/CTLA4-Ig/pxf3

```
                            SEQUENCE LISTING (1) GENERAL INFORMATION:

(iii) NUMBER OF SEQUENCES:         12

(2) INFORMATION FOR SEQ ID NO:    1:

(i) SEQUENCE CHARACTERISTICS:
            (A) LENGTH:                25
            (B) TYPE:                  nucleic acid
            (C) STRANDEDNESS:          single
            (D) TOPOLOGY:              linear (xi) SEQUENCE DESCRIPTION: SEQ ID NO: 1:

TGATGGACCT ACAGGAGCTC CTGAG                                           25

(2) INFORMATION FOR SEQ ID NO:    2:

(i) SEQUENCE CHARACTERISTICS:
            (A) LENGTH:                26
            (B) TYPE:                  nucleic acid
            (C) STRANDEDNESS:          single
            (D) TOPOLOGY:              linear (xi) SEQUENCE DESCRIPTION: SEQ ID NO: 2:

GAGTCAAATC CAGAAACATG CCGCAG                                          26

(2) INFORMATION FOR SEQ ID NO:    3:

(i) SEQUENCE CHARACTERISTICS:
            (A) LENGTH:                25
            (B) TYPE:                  nucleic acid
            (C) STRANDEDNESS:          single
            (D) TOPOLOGY:              linear (xi) SEQUENCE DESCRIPTION: SEQ ID NO: 3:

CGAAGAACAC CACAGAGAGT GAGCT                                           25

(2) INFORMATION FOR SEQ ID NO:    4:

(i) SEQUENCE CHARACTERISTICS:
            (A) LENGTH:                25
            (B) TYPE:                  nucleic acid
            (C) STRANDEDNESS:          single
            (D) TOPOLOGY:              linear (xi) SEQUENCE DESCRIPTION: SEQ ID NO: 4:

GACTCATTCA TGGTGCAGCT TATCG                                           25

(2) INFORMATION FOR SEQ ID NO:    5:

(i) SEQUENCE CHARACTERISTICS:
            (A) LENGTH:                25
            (B) TYPE:                  nucleic acid
            (C) STRANDEDNESS:          single
            (D) TOPOLOGY:              linear
```

(xi) SEQUENCE DESCRIPTION: SEQ ID NO: 5:

TGGAGTCACA GAAGGAGTGG CTAAG                                              25

(2) INFORMATION FOR SEQ ID NO:    6:

(i) SEQUENCE CHARACTERISTICS:
        (A) LENGTH:            25
        (B) TYPE:              nucleic acid
        (C) STRANDEDNESS:      single
        (D) TOPOLOGY:          linear (xi) SEQUENCE DESCRIPTION: SEQ ID NO: 6:

TCTGACCACA GTGAGGAATG TCCAC                                              25

(2) INFORMATION FOR SEQ ID NO:    7:

(i) SEQUENCE CHARACTERISTICS:
        (A) LENGTH:            31
        (B) TYPE:              nucleic acid
        (C) STRANDEDNESS:      single
        (D) TOPOLOGY:          linear (xi) SEQUENCE DESCRIPTION: SEQ ID NO: 7:

AGCGGCTGAC TGAACTGAAC TCAGATTGTA G                                       31

(2) INFORMATION FOR SEQ ID NO:    8:

(i) SEQUENCE CHARACTERISTICS:
        (A) LENGTH:            24
        (B) TYPE:              nucleic acid
        (C) STRANDEDNESS:      single
        (D) TOPOLOGY:          linear (xi) SEQUENCE DESCRIPTION: SEQ ID NO: 8:

GTCACAGTTT TCAGCTGTAT AGGG                                               24

(2) INFORMATION FOR SEQ ID NO:    9:

(i) SEQUENCE CHARACTERISTICS:
        (A) LENGTH:            24
        (B) TYPE:              nucleic acid
        (C) STRANDEDNESS:      single
        (D) TOPOLOGY:          linear (xi) SEQUENCE DESCRIPTION: SEQ ID NO: 9:

GGCAGGTCTA CTTTGGAGTC ATTG                                               24

(2) INFORMATION FOR SEQ ID NO:    10:

(i) SEQUENCE CHARACTERISTICS:
        (A) LENGTH:            26
        (B) TYPE:              nucleic acid
        (C) STRANDEDNESS:      single
        (D) TOPOLOGY:          linear (xi) SEQUENCE DESCRIPTION: SEQ ID NO: 10:

ACATTCGAGG CTCCAGTGAA TTCCAG                                             26

(2) INFORMATION FOR SEQ ID NO:    11:

(i) SEQUENCE CHARACTERISTICS:
        (A) LENGTH:            20
        (B) TYPE:              nucleic acid
        (C) STRANDEDNESS:      single
        (D) TOPOLOGY:          linear (xi) SEQUENCE DESCRIPTION: SEQ ID NO: 11:

```
AAGTGGATCC ACGAGCCCAA                                              20

(2) INFORMATION FOR SEQ ID NO:    12:

(i) SEQUENCE CHARACTERISTICS:
        (A) LENGTH:                20
        (B) TYPE:                  nucleic acid
        (C) STRANDEDNESS:          single
        (D) TOPOLOGY:              linear (xi) SEQUENCE DESCRIPTION: SEQ ID NO: 12:

CTGCACTTGC AGGAGCGCAC                                              20
```

METHODS AND COMPOUNDS FOR PREVENTION OF GRAFT REJECTION

This application is a continuation-in-part of U.S. patent application Ser. No. 08/024,569, filed Mar. 1, 1993 by Terry Strom, Vicki E. Rubin-Kelley, Towia Libermann entitled "Methods and Compounds for Prevention of Graft Rejection" now abandoned; which is a continuation-in-part of U.S. patent application Ser. No. 07/843,731, filed Feb. 28, 1992, now abandoned.

STATEMENT AS TO FEDERALLY SPONSORED RESEARCH

This work was funded in part by National Institutes of Health grants PODK 40839, DK 36149, and P50DK39249 from the U.S. Government, which therefore has certain rights in the invention.

FIELD OF THE INVENTION

This invention relates to methods and compounds useful in inhibiting the immune response in a mammal.

BACKGROUND OF THE INVENTION

For many life-threatening diseases, organ transplantation is considered a standard treatment and, in many cases, the only alternative to certain death. The immune response to foreign cell surface antigens on the graft, encoded by the major histocompatibility complex (MHC) and present on all cells, generally precludes successful transplantation of tissues and organs unless the transplant tissues come from a compatible donor or the normal immune response is suppressed. The best compatibility and thus, long term rates of engraftment, are achieved using MHC identical sibling donors or MHC identical unrelated cadaver donors (Strom, 1989, supra; Strom, 1990, *Clinical Aspects of Autoimmunity* 4:8–19).

The host response to an organ allograft involves a complex series of cellular interactions among T and B lymphocytes as well as macrophages or dendritic cells that recognize and are activated by a foreign antigen (Strom, 1989, supra; Strom, 1990, *Clinical Aspects of Autoimmunity* 4:8–19). Co-stimulatory factors, primarily cytokines, and specific cell—cell interactions, provided by activated accessory cells such as macrophages or dendritic cells are essential for T cell proliferation. These macrophages and dendritic cells either directly adhere to T cells through specific adhesion proteins or secrete cytokines that stimulate T cells, such as IL-1 and IL-6 (Strom, 1989, *In: Organ Transplantation: Current Clinical and Immunological Concepts:* 4:8–19; Strom, 1990, *Clinical Aspects of Autoimmunity* 4:8–19).

IL-1 induces expression of the IL-6 gene in accessory cells. Accessory cell-derived co-stimulatory signals stimulate activation of interleukin-2 (IL-2) gene transcription and expression of high affinity IL-2 receptors in T cells (Pankewycz, et al., 1989 *Transplantation* 47:318; Cantrell, et al., *Science* 224:1312; Williams, et al., 1984 *J. Immunol.* 132:2330–2337). IL-2, a 15 kDa protein, is secreted by T lymphocytes upon antigen stimulation and is required for normal immune responsiveness. IL-2 stimulates lymphoid cells to proliferate and differentiate by binding to IL-2 specific cell surface receptors (IL-2R). IL-2 also initiates helper cell activation of cytotoxic T cells and stimulates secretion of γ-interferon (γ-IFN) which in turn activates cytodestructive properties of macrophages (Farrar, et al., 1981 *J. Immunol.* 126:1120–1125). Furthermore, γ-IFN and IL-4 are also important activators of MHC class II expression in the transplanted organ, thereby further expanding the rejection cascade by actually making the grafted organ more immunogenic (Pober, et al., 1983, *J. Exp. Med.,* 157:1339; Kelley, et al., 1984 *J. Immunol.,* 132:240–245).

Similar mechanisms are involved in the development of autoimmune disease, such as type I diabetes. In humans and non-obese diabetic mice (NOD), insulin-dependent diabetes mellitus (IDDM) results from a spontaneous T-cell dependent autoimmune destruction of insulin-producing pancreatic β cells that intensifies with age. The process is preceded by infiltration of the islets with mononuclear cells (insulitis), primarily composed of T lymphocytes (Bottazzo, G. F., et al., 1985, *J. Engl. J. Med.,* 113:353; Miyazaki, A., et al., 1985, *Clin. Exp. Immunol.,* 60:622). A delicate balance between autoaggressive T-cells and suppressor-type immune phenomena determine whether expression of autoimmunity is limited to insulitis or progresses to IDDM. In NOD mice, a model of human IDDM, therapeutic strategies that target T-cells have been successful in preventing IDDM (Makino, et al., 1980, *Exp. Anim.,* 29:1). These include neonatal thymectomy, administration of cyclosporine A, and infusion of anti-pan T-cell, anti-CD4, or anti-CD25 (IL-2R) mAbs (Tarui, et al., 1986, *Insulitis and Type I Diabetes. Lessons from the NOD Mouse.* Academic Press, Tokyo, p. 143).

The aim of all rejection prevention and reversal strategies is to suppress the patient's immune reactivity to the graft, with a minimum of morbidity and mortality. Existing immunosuppressive therapies include administration of immunosuppressive compounds such as cyclosporine A, FK506 and rapamycin (First, 1992 *Transplantation,* 53:1–11). Because these agents inhibit proliferation of T cells generally, systemic treatment of patients leads to systemic immunosuppression which carries with it potential complications, including increase risk of infections and cancer (Wilkinson, et al., *Transplant,* 47:293–296; Penn, 1991 *Transplant Proc.,* 23:1101; Beveridge, et al., 1984 *Lancet,* 1:788). In addition, these immunosuppressive agents cause considerable side effects, including nephrotoxicity, hepatotoxicity, hypertension, hirsutism, and neurotoxicity (Strom, 1989, supra; Strom, 1990, *Clinical Aspects of Autoimmunity,* 4:8–19; Tilney, et al., 1991 *Ann Surg.,* 214:42–49; Myers, et al., 1984 *N. Engl. J. Med.,* 311:699).

Administration of monoclonal antibodies against the T cell-specific antigen CD3 has been shown to block acute allograft rejection (Mackie, et al., 1990 *Transplantation,* 49:1150). Antibodies directed against the IL-2 receptor, T cell receptor, CD4, and certain cell adhesion molecules such as ICAM-1 have been used (Cosimi, et al., 1990 *Surgery,* 108:406; Cosimi, et al., 1990 *J. Immunol.,* 144:4604; Strom et al., 1989 *Kidney Int.,* 35:1026; Walz, 1990 *Transplantation,* 49:198–201). Anti-IL-2 receptor antibodies have been shown to bring about improved patient and graft survival (Soulillou, et al., 1990 *N. Engl. J. Med.,* 322:1175).

Two novel cytokines, TGF-β and IL-10, have recently been identified. These proteins have immunosuppressive activity, and apparently act via different mechanisms on the immune system (Moore, et al., 1990 *Science,* 248:1230–1234; Vieira, et al., 1991 *Proc. Natl. Acad. Sci USA,* 88:1172–1176; Barnard, et al., 1990 *Biochim Biophys. Acta,* 1032:79–87; Derynck, et al., 1985 *Nature,* 316:701–705).

TGF-β exhibits potent immunosuppressive effects including inhibition of B and T cell activation and differentiation and deactivation of activated macrophages (Barnard, et al., 1990 Biochim Biophys. Acta, 1032:79–87; Roberts et al., 1990 Handbook of Experimental Pharmacology, 95:419–472). In particular, TGF-β inhibits expression of immunoglobulin genes in B cells, decreases IL-2 induced T cell proliferation and differentiation of cytotoxic T cells, and inhibits MHC class II antigen expression on a number of cell types (Kehrl, et al., 1986 J. Exp. Med., 163:1037–1050; Ruegemer, et al., 1990 J. Immunol., 144:1767–1776; Cross, et al., 1990 J. Immunol., 144:432–439; Nelson, et al., 1991 J. Immunol., 146:1849–1857; Lee, et al., 1987 J. Exp. Med., 166:1290–1299; Wright, et al., 1986 Diabetes, 353:1174–1177). TGF-β has been shown to inhibit pancreatic islet allograft rejection in mice, suggesting its potential use as an immunosuppressive agent. TGF-β is produced by many different cell types, including macrophages, B and T cells, lung and mesenchymal cells, skin cells, platelets, and bone cells (Barnard, et al., 1990 Biochim Biophys. Acta, 1032:79–87; Roberts et al., 1990 Handbook of Experimental Pharmacology, 95:419–472). In addition, some cancer patients have been observed to show signs of immunosuppression due to secretion of TGF-β by the cancer cells (Barnard, et al., 1990 Biochim Biophys. Acta, 1032:79–87; Roberts et al., 1990 Handbook of Experimental Pharmacology, 95:419–472; Siepl, et al., 1988 Eur. J. Immunol., 18:593–600).

IL-10 was first identified as a product of activated $T_H2$ T helper cells with the ability to inhibit macrophage-dependent cytokine synthesis in $T_H1$ T helper cells (Fiorentino, et al., 1989 J. Exp. Med., 170:2081). IL-10 appears to be expressed by several different hematopoietic cell types, including activated $T_H2$ cells, activated macrophages, mast cells, and B cells (Moore, et al., 1990 Science, 248:1230–1234; O'Barra, et al., 1990 Int. Immunol., 2:821; De Waal Malefyt, et al., 1991 J. Exp. Med., 174:1209–1220). IL-10 appears to inhibit the expression of a number of cytokines in macrophages, including interleukin-6 (IL-6), interleukin-1 (IL-1), interleukin-8 (IL-8), tumor necrosis factor-α (TNF-α), granulocyte/macrophage colony stimulatory factor (GM-CSF) and granulocyte colony stimulatory factor (G-CSF). IL-10 diminishes the antigen-presenting capacity of macrophages via downregulation of MHC class II gene expression on macrophages, and induces expression of MHC class II genes, but not class I genes in unstimulated splenic B cells (Go, et al., 1990 J. Exp. Med., 172:1625–1631; De Waal Malefyt, et al., 1991 J. Exp. Med., 174:915–924).

SUMMARY OF THE INVENTION

We have developed novel methods for achieving localized immunosuppression. These methods may be used for the prevention of graft rejection following organ or tissue transplantation and for the prevention of tissue destruction due to autoimmune disease. Our methods allow strong local immunosuppression without the side effects associated with general immunosuppressive methods now in use. In addition to these methods, we have discovered a new immunosuppressive protein.

Accordingly, in one aspect, the invention features a method for inhibiting rejection of a transplanted tissue in a mammal, involving (a) introducing into a cell, either in vivo or ex vivo, DNA encoding an immunosuppressive protein such that the cell expresses (and preferably secretes) the immunosuppressive protein. If the DNA is introduced ex vivo, the method further includes transplanting the cell into the mammal. The cell may be a cell of the transplanted tissue or organ or may be a cell to be transplanted to the region of the body near the transplanted tissue organ. The immunosuppressive protein is, according to the invention, produced in the localized anatomical region where it is required, i.e., in the vicinity of the transplanted tissue, but is not administered systemically to the animal. Thus, generalized systemic immunosuppressive effects are not produced. This localized expression is achieved by providing the DNA encoding the immunosuppressive protein under the regulatory control of a promoter sequence not naturally found immediately 5' to the immunosuppressive polypeptide-encoding DNA. The promotor may be constitutive, tissue-specific, immune response inducible, or inducible by orally or systemically administered compounds.

The method can be used to inhibit rejection of both allografts and xenografts, e.g., transplanted organs such as heart, kidney, liver and lung, and tissues such as bone and skin, or cellular transplants, e.g., islets.

In a second aspect, the invention features a method for inhibiting tissue damage due to autoimmune disease in a mammal by introducing into a cell, either in vivo or ex vivo DNA encoding the immunosuppressive protein such that the cell expresses (and preferably secretes) the immunosuppressive protein. Where the DNA is introduced ex vivo, the method further includes transplantation of the tissue into the mammal. Using either method of introduction, the immunosuppressive protein is expressed (and preferably secreted) by the cell of the tissue at levels sufficient to produce an immunosuppressive effect. The local expression of the immunosuppressive protein is achieved by providing the DNA encoding the immunosuppressive protein under the regulatory control of a promoter not naturally found immediately 5' to the DNA encoding the immunosuppressive protein. The immunosuppressive protein is, according to the invention, produced in the localized anatomical region where it is required, i.e., in the vicinity of the diseased or disease prone tissue or organ, but is not administered systemically to the animal, so that generalized systemic immunosuppressive effects are not produced.

The method can be used to decrease autoimmune damage to organs such as heart, kidney, liver, and lung, and to tissues such as bone, skin, neuronal tissue, and synovium.

Both the methods of transplant rejection inhibition and the inhibition of autoimmune related tissue destruction involve localized suppression of the immune response. These methods can employ DNA which encodes any immunosuppressive protein. Examples of suitable proteins are interleukin-10 (IL-10), transforming growth factor β(TGF-β), and the suppressor factor described below produced by human T-cell clones such as IS-2.15. Also included are genes encoding immunosuppressive fusion proteins, such as IL-2Ig, CD2Ig, CTLA-4Ig wherein the N-terminus includes amino acids present in human IL-2, CD-2 or CTLA-4 and the C-terminus includes amino acids present in the Fc fragment of the Ig heavy chains. These proteins all directly decrease the immunosuppressive response in the region where they are expressed.

In a third aspect, the methods of the invention can also employ DNA encoding a protein which indirectly acts as an immunosuppressant. For example, the method may employ the use of a transgene which encodes cyclosporine synthetase. Thus, the cyclosporine synthetase locally processes cyclosporine precursor molecules into the immunosuppressant compound, cyclosporine. In another embodiment, DNA encoding a polypeptide which metabolizes cyclophosphamide to the active form may also be provided using the methods of the invention. Where DNA encoding a protein that processes a prodrug to yield an active immunosuppressant is employed, the method also features the subsequent administration of the prodrug. As with directly immunosuppressive polypeptides, use of a DNA construct expressing a peptide which acts indirectly creates local immunosuppression without the systemic side effects of general immunosuppression.

In a fourth aspect, DNA encoding a glycosidase may be provided to cells in the region where immunosuppression is desired. Synthesis of such a protein will locally remove antigenic determinants which are targets for xenoreactive natural antibodies.

Expression of directly or indirectly immunosuppressive proteins or glycosidases in the cells in or near the transplanted tissue or in the area of autoimmune response can be controlled by regulatory sequences which cause constitutive expression, or alternatively, expression can be controlled by regulatory sequences which are inducible; in one preferred embodiment, the regulatory sequence controlling expression of the immunosuppressive protein is inducible by a compound which stimulates an immune response. For example, the promoter can be inducible by IL-1, which is expressed during activation of responses. Thus, responses that cause rejection of the transplanted organ or destruction of the autoimmune target tissue when the immune system is being stimulated to cause a rejection turns on the gene for the immunosuppressive protein and halts or slows rejection. Alternatively, the promoter controlling transcription of the immunosuppressive protein gene is inducible by a foreign antigen of the transplanted tissue itself; in this case, as well, the same component which tends to cause rejection also turns down expression of the protein inhibiting rejection.

Promoters which may be used for the expression of the immunosuppressive proteins or glycosidases of the invention are shown in Table 1. In one embodiment, the regulatory sequence controlling expression of the immunosuppressive protein contains a binding site for a non-mammalian (e.g. bacterial) inducible regulator. In this embodiment DNA encoding constitutively expressed non-mammalian regulatory protein is also provided. The DNA encoding the regulatory protein may be provided as a part of the DNA sequences encoding the immunosuppressive protein or they may be provided in a second construct. In this embodiment, the inducer is then provided separately, preferably orally, as needed to prevent graft rejection or autoimmune mediated tissue destruction. Thus, the positive bacterial regulatory gene NAHR encodes a factor which activates the PG promotor only in the presence of Na-Salicylate (Yen. *J. Bacteriol.*, 173:5328–35 (1991), incorporated herein by reference).

Preferred promoter-gene combinations for the treatment of a graft rejection of various tissues are shown in Table 2, top. Preferred promoter-gene constructs for the treatment of specific autoimmune diseases are shown in Table 2, bottom. In addition, constructs are shown in FIGS. 10–15. These constructs may be used to express immunosuppressive proteins other than those specifically depicted.

The methods of the invention may be used alone for the treatment of autoimmune disease or graft rejection or they may be used in combination with other immunosuppressive therapies.

Constructs of the invention which are immunosuppressive, as used herein, are those constructs which prolong engraftment beyond the 50% rejection period for the control animal similarly treated, but lacking the transgene. For example, constructs which include non-specific constitutive, immune-responsive, inducible, or pancreatic β-cell specific promoters may be tested in the pancreatic islet cell transplant model described below. Tissue specific expression may be tested in transgenic mice containing the appropriate promotor constructs. Once the mouse is constructed, expression is tested by reverse transcriptase polymerase chain reaction and Northern blot hybridization using RNA and DNA isolated from different mouse tissues and organs. Constructs for use in the treatment of autoimmune disease are also defined as those which show at least a 20% decrease in tissue damage relative to a control lacking the therapy over a period of time required for complete disease progression in the appropriate mouse model. For example, since with or without the lpr gene, NOD mice and EAE model mice may be used to choose among constructs for use in the methods of invention. These mice are already publicly available from suppliers such as Jackson Labs, Bar Harbor, Me. Useful constructs are also those which provide a mixed lymphocyte reaction (MLR) by decreasing proliferation by 20%, more preferably 40%, and most preferably, by 60% relative to control cells not expressing the transgene. This assay may be done as described in *Current Protocols in Immunology* (1992, Wiley & Sons, Eds., Coligan et al.).

In a fifth aspect, the invention features a substantially pure suppressor factor protein or biologically active analog or fragment thereof. The protein is characterized in that it is secreted by cloned anergic T-cells (e.g., IS-2.15 cells), it blocks interleukin 2 (IL-2)-stimulated T-cell proliferation, it has an apparent molecular weight of between 10 and 30 kilodaltons, it can be inactivated by heating to 65° C. for 15 minutes, it blocks interleukin 4 (IL-4)-stimulated T-cell proliferation in vitro, it is non-cytotoxic to T-cells, and it does not inhibit the production of IL-2 by T-cells in vitro.

"Anergic T-cells", as used herein, refers to T-cells that are hyporesponsive or unresponsive to an antigen or mitogen. By "apparent molecular weight" is meant molecular weight as determined by filtration through microconcentrator tubes with multiple membrane size cut-offs, followed by testing of the resulting concentrates and filtrates for T-cell suppressor activity as described in the detailed description to follow.

The invention also features a purified nucleic acid encoding the new suppressor factor of the invention.

The nucleic acid of the invention can be used to alter the effect of IL-2 on cells in a mammal that express, constitutively or transiently, the IL-2 receptor, in order to inhibit IL-2 induced cell proliferation, the proliferation of autoreactive T-cells. The method involves bringing into close proximity of the cell a second cell which is transfected with the nucleic acid encoding the suppressor factor, so that the second cell secretes a protein which causes an alteration of the IL-2 effect. The mammal is preferably a human, and the cell is preferably a T-cell, an endothelial cell lining a blood vessel, or an epithelial cell, most preferably an epithelial cell of the kidney proximal tubule, or an epithelial cell of the gut.

The nucleic acid of the invention can also be used to alter the effect of IL-2 on cells in a mammal that express, constitutively or transiently, the IL-2 receptor. The method involves transfecting the cell with the nucleic acid so that the cell secretes the suppressor factor, causing alteration of the IL-2 effect.

In a related aspect, the invention features a method of altering the effect of IL-4 on cells in a mammal that express, constitutively or transiently, the IL-4 receptor, in order to inhibit IL-4 induced cell proliferation. The method involves bringing into close proximity of the cell a second cell which is transfected with the nucleic acid encoding the suppressor factor, so that the second cell secretes the factor causing an alteration of the IL-4 effect. The mammal is preferably a human, and the cell is preferably a T-cell, an endothelial cell lining a blood vessel, or an epithelial cell, most preferably an epithelial cell of the kidney proximal tubule, or an epithelial cell of the gut.

In a another aspect, the nucleic acid of the invention can be used in a method of altering the effect of IL-4 on cells in a mammal that express, constitutively or transiently, the IL-4 receptor. The method involves transfecting the cell with the nucleic acid encoding the suppressor factor so that the cell secretes the factor causing alteration of the IL-4 effect.

The suppressor factor protein of the invention can be obtained from any suitable naturally occurring source and can also be made recombinantly. Also included in the invention are biologically active fragments and analogs of the suppressor factor. The term "fragment", as applied to a polypeptide, will ordinarily be at least about 10 contiguous amino acids, more typically at least about 20 contiguous amino acids, usually at least about 30 contiguous amino acids, preferably at least about 40 contiguous amino acids, more preferably at least about 50 contiguous amino acids, and most preferably at least about 60 to 80 or more contiguous amino acids in length. Biologically active fragments of the suppressor factor can be generated by methods known to those skilled in the art.

A suppressor factor polypeptide, fragment, or analog is biologically active if it exhibits a biological activity of naturally occurring IS-2.15 suppressor factor, e.g., the ability to block IL-2 stimulated T-cell proliferation. The ability of a candidate analog or fragment to block IL-2 stimulated T-cell proliferation can be assessed by methods known to those skilled in the art, e.g., by methods described below or above, such as the islet transplant rejection assay or the MCR assay.

The invention also includes biologically active analogs of the suppressor factor protein of the invention. Analogs can differ from naturally occurring IS-2.15 suppressor factor by amino acid sequence differences or by modifications that do not affect sequence, or by both. Modifications include in vivo or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to enzymes that affect glycosylation derived from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine.

Analogs can differ from naturally occurring IS-2.15 suppressor factor by alterations of their primary sequence. These include genetic variants, both natural and induced. Induced mutants may be derived by various techniques, including random mutagenesis of the encoding nucleic acids using irradiation or exposure to ethanemethylsulfate (EMS), or may incorporate changes produced by site-specific mutagenesis or other techniques of molecular biology. See, Sambrook, Fritsch and Maniatis (1989), *Molecular Cloning: A Laboratory Manual* (2d ed.), CSH Press, hereby incorporated by reference. Also included are analogs that include residues other than naturally occurring L-amino acids, e.g., D-amino acids or non-naturally occurring or synthetic amino acids, e.g., β or γ amino acids.

Analogs of the invention, to be biologically active, will generally exhibit at least 70%, more preferably 80%, more preferably 90%, and most preferably 95% or 99%, homology with all or part of a naturally occurring IS-2.15 suppressor factor amino acid sequence. The length of comparison sequences will generally be at least about 8 amino acid residues, usually at least 20 amino acid residues, more usually at least 24 amino acid residues, typically at least 28 amino acid residues, and preferably more than 35 amino acid residues.

"Homologous", or "homology", as used herein, refers to the subunit sequence similarity between two polymeric molecules, e.g., between two nucleic acid molecules, e.g., two DNA molecules, or two polypeptide molecules. When a subunit position in both of the two molecules is occupied by the same monomeric subunit then they are homologous at that position. The homology between two sequences is a direct function of the number of matching or homologous positions, e.g., if half, e.g., 5 of 10, of the positions in two compound sequences are homologous then the two sequences are 50% homologous, if 90% of the positions, e.g., 9 of 10, are matched or homologous the two sequences share 90% homology. By way of example, the DNA sequences 3'ATTGCC'5 and 3'TATGGC'5 are 50% homologous.

The invention also includes proteins encoded by DNA that hybridizes to IS-2.15 suppressor factor-encoding nucleic acids, and polypeptides or proteins specifically bound by antisera to IS-2.15 suppressor factor, e.g., antisera to the active site or binding domain of IS-2.15 suppressor factor.

The invention also includes polypeptides that differ from the naturally-occurring suppressor factor by substitution of one amino acid for another of the same class, or that differ by one or more non-conservative amino acid substitutions, deletions, or insertions, located at positions of the amino acid sequence that do not destroy the biological activity of the polypeptide. Amino acids of the same class are ones that share characteristics of hydrophobicity, charge, pKa, or other conformational or chemical properties (e.g., valine for glycine, arginine for lysine, etc.)

As used herein, the term "substantially pure" describes a protein, e.g., an IS-2.15 suppressor factor protein or polypeptide, that has been separated from the components that it is naturally associated with i.e., the components of a eukaryotic cell. Typically, a protein is substantially pure when at least 60%, more preferably at least 75%, more preferably at least 90%, and most preferably at least 99%, of the total material (by volume, by wet or dry weight, or by mole per cent or mole fraction) in a sample is the compound of interest. Purity can be measured by any appropriate method, e.g., in the case of polypeptides by column chromatography, polyacrylamide gel electrophoresis, or HPLC analysis.

A "purified nucleic acid", as used herein, refers to a nucleic acid sequence or fragment that is not associated with the sequences that flank it in a naturally occurring state, e.g., a DNA fragment that has been removed from the sequences that are adjacent to the fragment, e.g., the sequences adjacent to the fragment in its normal site in the genome. The term also applies to nucleic acids that have been substantially purified from other components that naturally accompany it in the cell, and also applies to cDNA and synthetic nucleic acids.

The properties of the suppressor factor of the invention render it and its biologically active analogs and fragments useful in a number of therapeutic and diagnostic applications. In therapy in particular, the factor, because of its immunosuppressive effects, may be useful in the treatment of autoimmune diseases such as lupus, type 1 diabetes, and rheumatoid arthritis. The factor may also be used to inhibit transplant rejection and graft versus host disease (GVHD) following transplantation. When used for this purpose, the suppressor factor will be administered generally by the same regimens, and in the same dosage range, as current commercially-available immunosuppressive agents, with the provision that, because the suppressor factor of the invention is a protein, it will preferably be administered intravenously rather than orally. A nucleic acid encoding the suppressor factor of the invention may be used to protect cells against autoreactive T-cells.

Other features and advantages of the invention will be apparent from the following detailed description thereof, and from the claims.

DETAILED DESCRIPTION

The drawings are first described.

DRAWINGS

Figure 1:
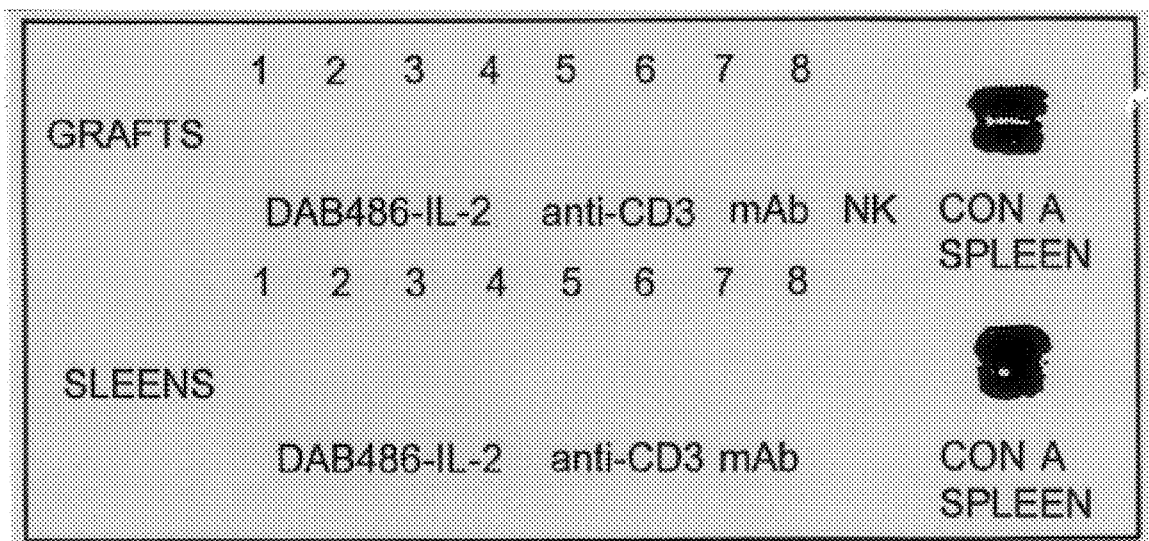

FIG. 1. is a Southern blot of products of a reverse transcriptase-polymerase chain reaction (RVT-PCR). RVT-PCR transcripts of IL-2 in islet cell grafts and spleens on day 8 post engraftment. Four mice were treated with DAB486-IL-2 (lanes 1–4) and four with anti-CD3 mAb (lanes 5–8) for 8 days. All harvested tissue was snap frozen in liquid nitrogen and total RNA extracted by the GCN method. Five $\mu$g of total RNA was used as starting material for RVT-PCR. Products were size separated on a 1.5% agarose gel to confirm the product size and blotted to a nylon membrane and probed with a cDNA labelled with $^{32}$P. The blots were then scanned using the PHOSPHOR IMAGER system (Molecular Dynamics Inc.) (NK Normal kidney).

Figure 2:
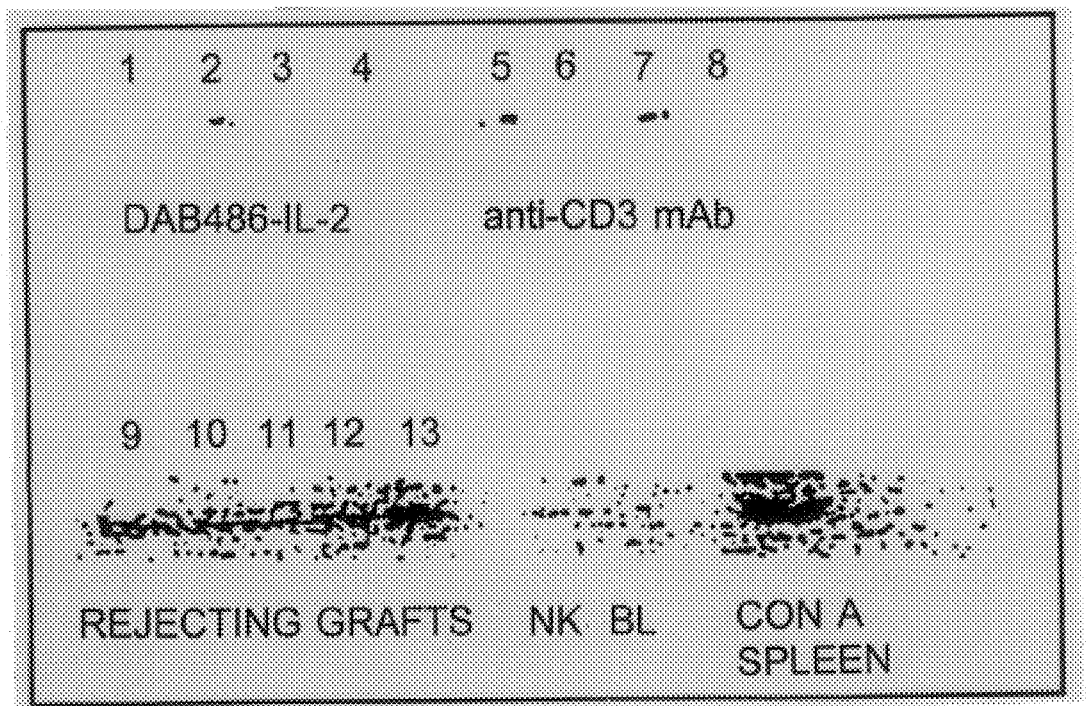

FIG. 2 is a Southern blot of PCR products. RVT-PCR transcripts of IFN Gamma in 5 rejecting grafts (lanes 9–13). 4 grafts treated with DAB-IL-2 (lanes 1–4) for 8 days and 4 grafts treated with anti-CD3 mAb (lanes 5–8) for 8 days. All grafts were harvested on day 8 post transplant, snap frozen in liquid nitrogen and processed for total RNA. Two $\mu$g of total RNA was used for RVT-PCR. Products were run on a 1.5% agarose gel and blotted to a nylon filter then hybridized with an IFN Gamma cDNA probe labelled with $^{32}$P. The blots were then scanned using the PHOSPOR IMAGER system (Molecular Dynamics Inc.) (NK normal kidney. BL blank.)

Figure 3:
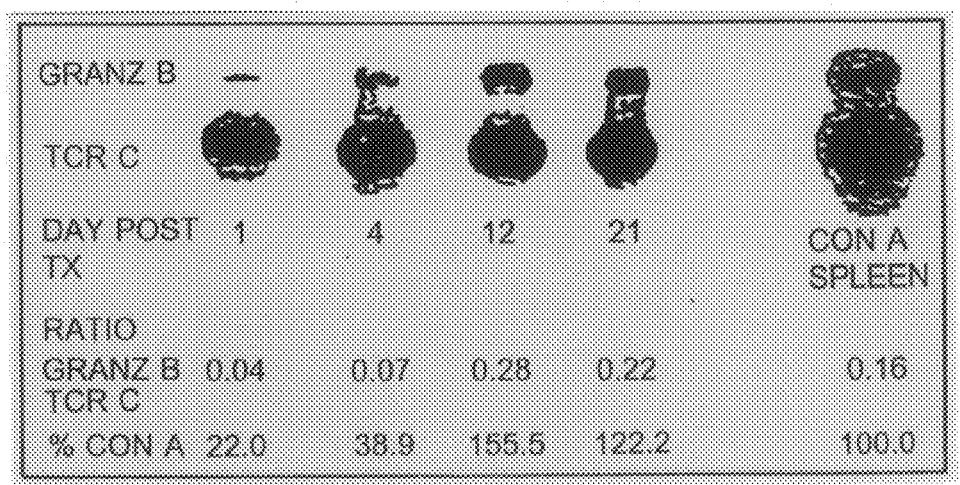

FIG. 3 is a Southern blot of PCR products. RVT-PCR products of coamplified GRANZYME B and TCR C$\alpha$ mRNA transcripts from spleens 1, 4, 12, 21 days post transplant, in rejecting model of pancreatic islet cell transplantation, and CON A stimulated spleen cells. One $\mu$g of total RNA per sample was used as starting material. The products were size separated on a 2.5% agarose gel, blotted to a nylon membrane and cohybridized with $^{32}$P labelled cDNA probes for GRANZYME B and TCR C$\alpha$. Using the PHOSPHOR IMAGER and IMAGEQUANT software (Molecular Dynamics Inc.) the bands were quantitated and expressed as a ratio of GRANZYME B to TCR C$\alpha$ as well as a percentage relative to the CON A control.

Figure 4A:
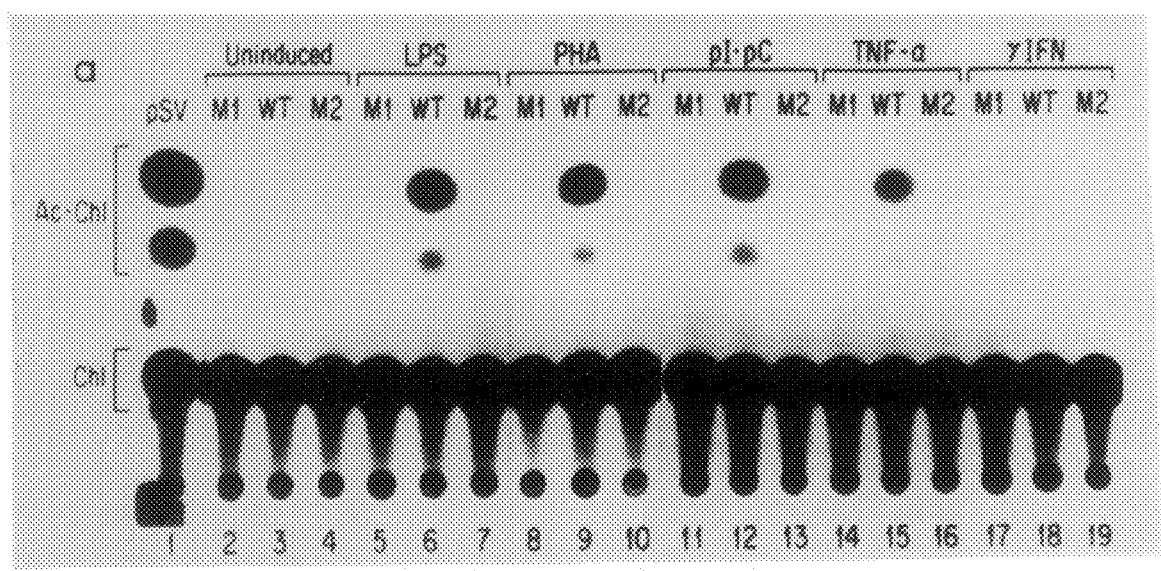

FIGS. 4a & b

FIG. 4a is an autoradiograph showing the results of CAT assays of extracts prepared from U-937 cells transfected with a 1.2 kb BamHI-XhoI IL-6-CAT construct containing wild-type (WT) (lane 3, 6, 9, 12, 15, and 18), mutant M1 (lanes 2, 5, 8, 11, 14, and 17), or mutant M2 (lanes 4, 7, 10, 13, 16 and 19) kB sites as illustrated in FIG. 1. The cells were either uninduced (lanes 2 to 4) or stimulated 33 h after transfection with 10 $\mu$g of LPS per ml (lanes 5 to 7). 2 $\mu$g of PHA per ml (lanes 8 to 10). 100 $\mu$g of double-stranded RNA poly(IC) (Pl-pC) per ml (lanes 14 to 16), or 100 units of IFN-$\gamma$ per ml (lanes 17 to 19) for 19 h.

Figure 4B:
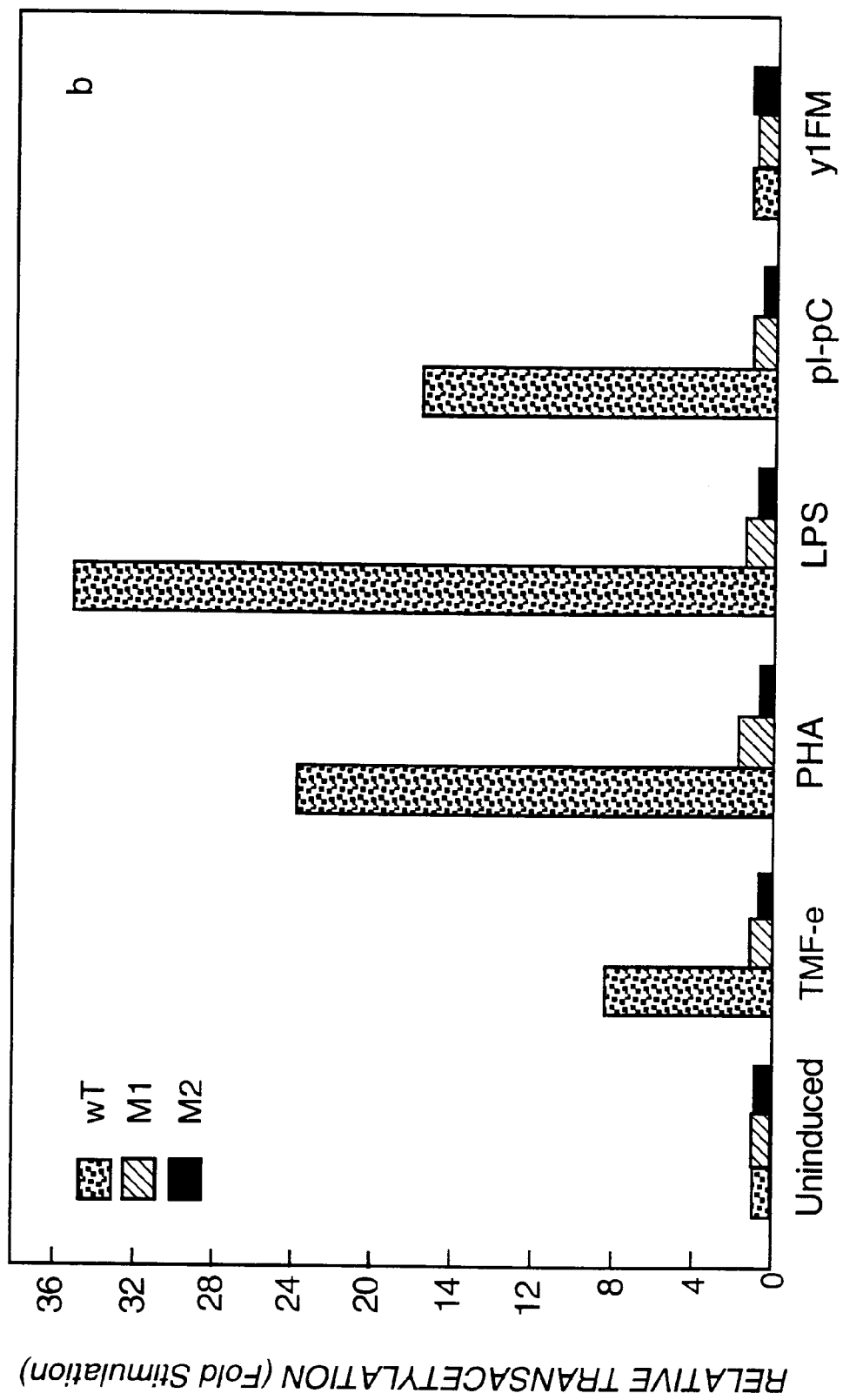

FIG. 4b is a graph of relative CAT activity after induction by various stimuli in U-937 cells. Acetylated and nonacetylated forms of chloramphenicol from the assay were quantitated by liquid scintillation counting. Values are represented as fold induction of the wild-type (WT) or mutant IL-6 promoter over CAT activity expressed in uninduced cells. Similar results were obtained in three independent experiments. Induction of IL-6-CAT expression in U-937 cells depends on an intact kB site.

Figure 5A:
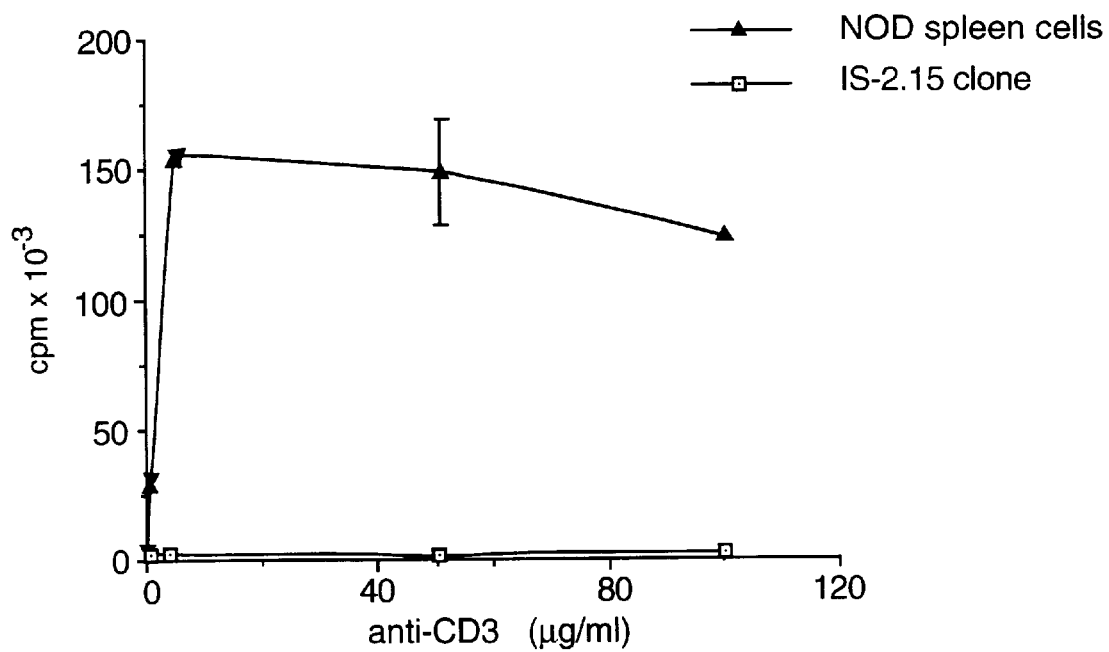
Figure 5B:
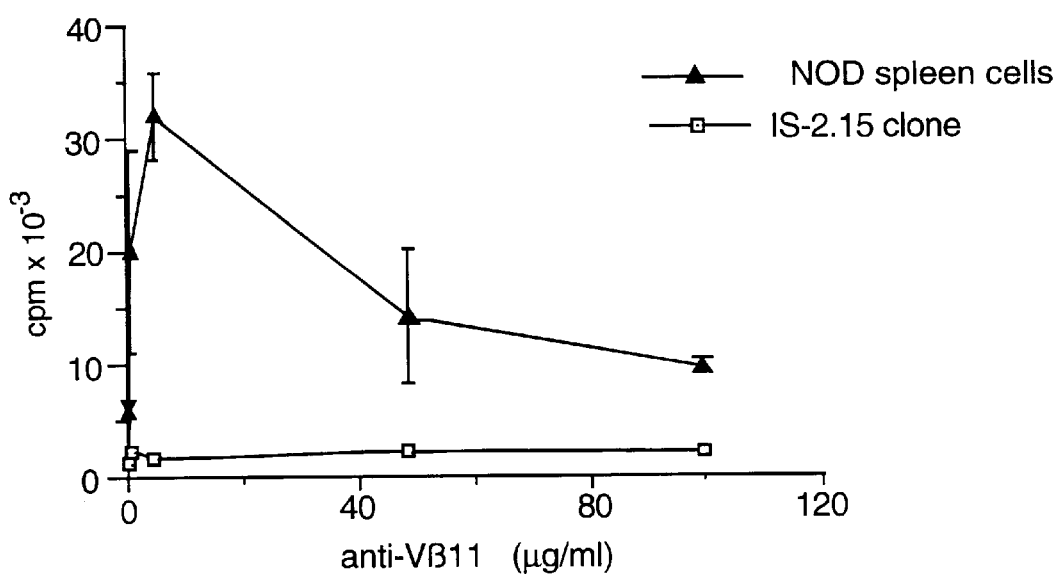
Figure 5C:
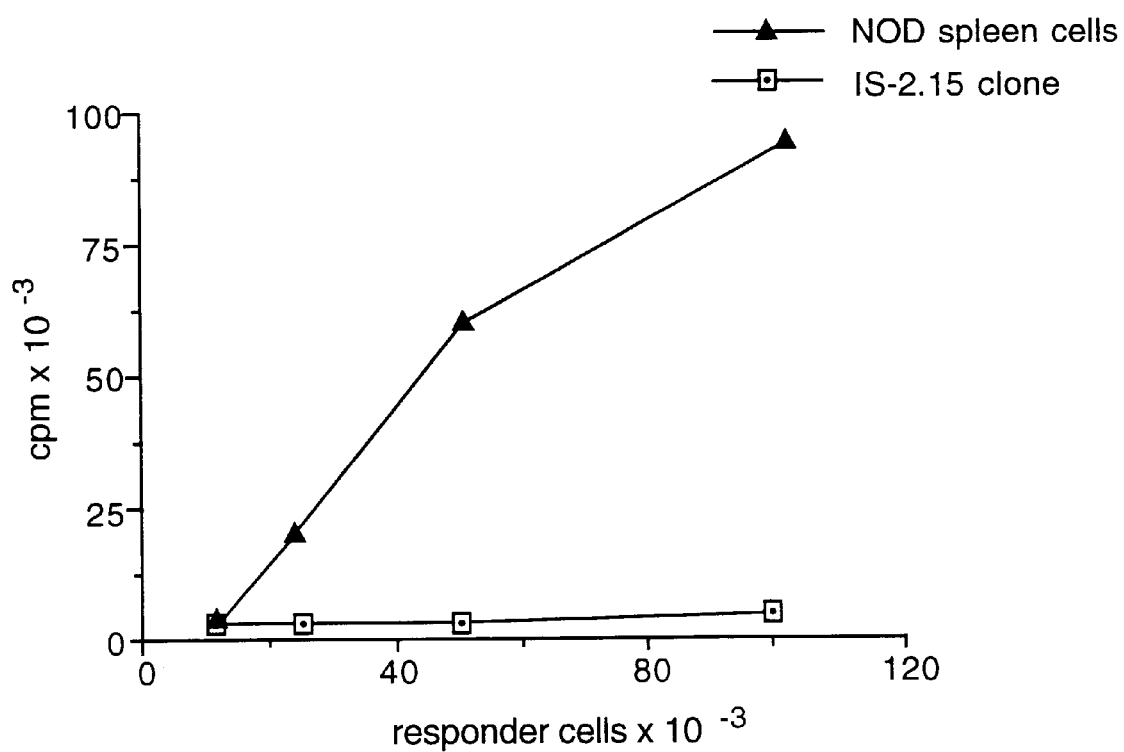

FIGS. 5A–C is a set of three graphs illustrating the effect of transforming growth factor (TGF) crosslinking on proliferation of the IS-2.15 clone. Each point represents the mean of triplicate determinations±SEM. As a positive control, the same experimental procedure was undertaken using $10^5$ NOD spleen cells.

Figure 6A:
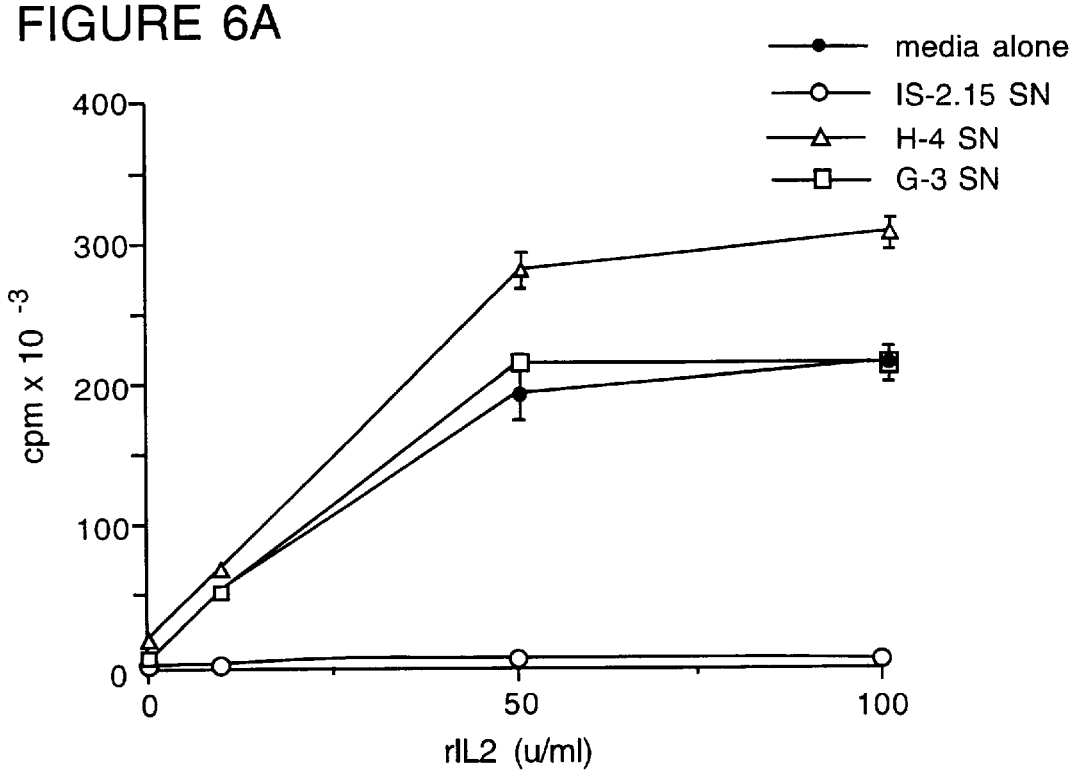
Figure 6B:
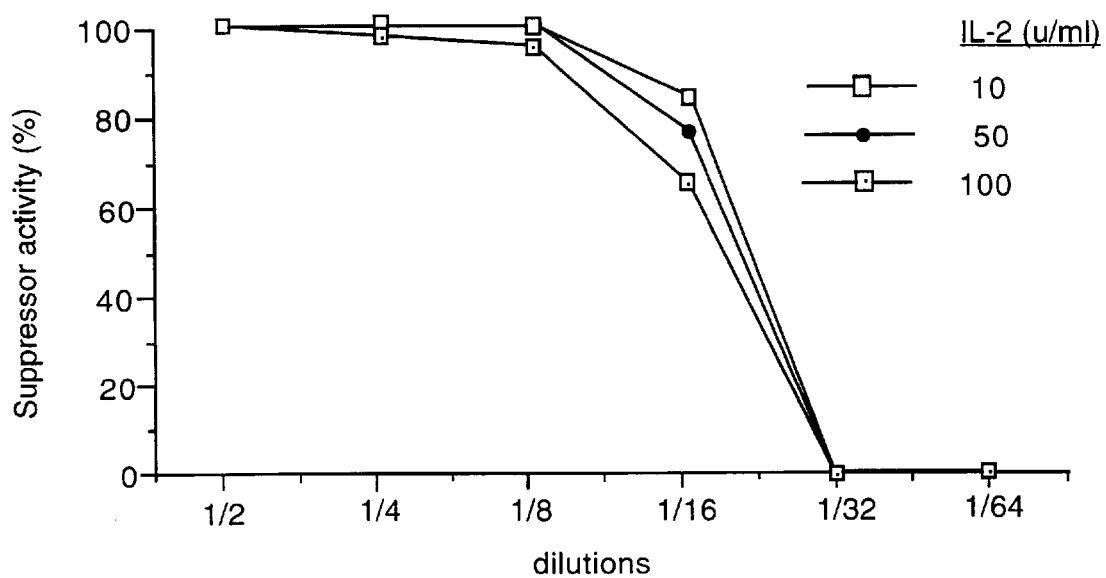

FIGS. 6A and 6B are a pair of graphs illustrating that IS-2.15 supernatant specifically inhibits IL-2 dependent proliferation in IL-2 dependent murine T-cell lines. FIG. 6A shows the effect of supernatant (50% final dilution) from 3 different clones upon T-cell proliferation. Each point represents mean±SEM of triplicate determinations. FIG. 6B represents the effect of titrating IS-2.15 supernatant versus different concentrations of IL-2.

Figure 7:
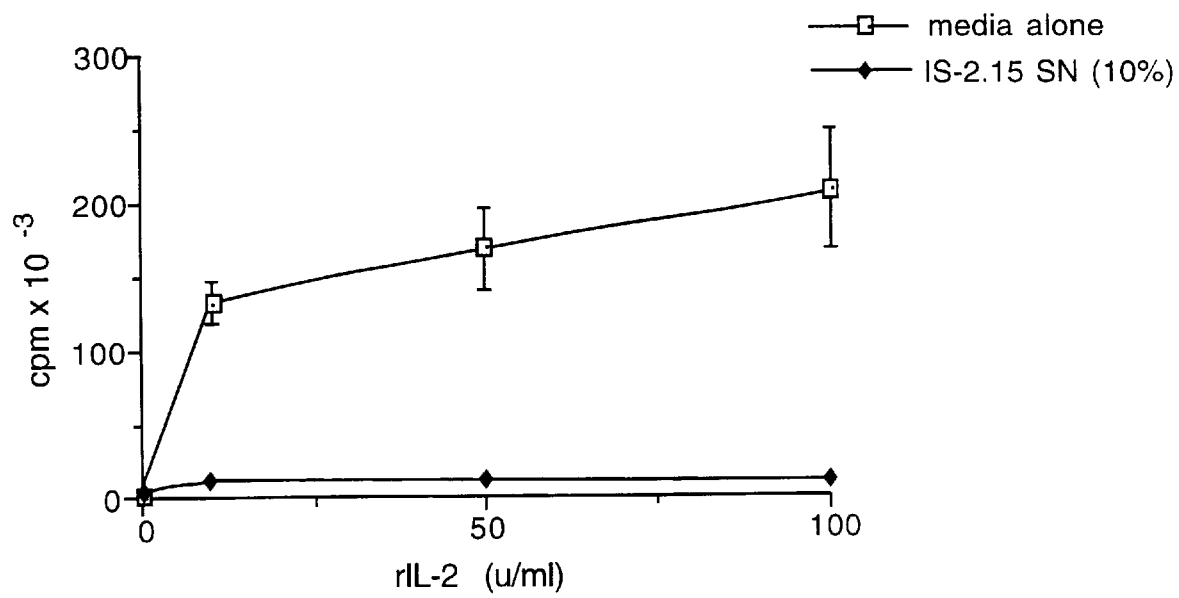

FIG. 7 is a graph illustrating that the inhibitory activity of IS-2.15 is not reversible. Results represent cpm±1 SD of triplicates.

Figure 8A:
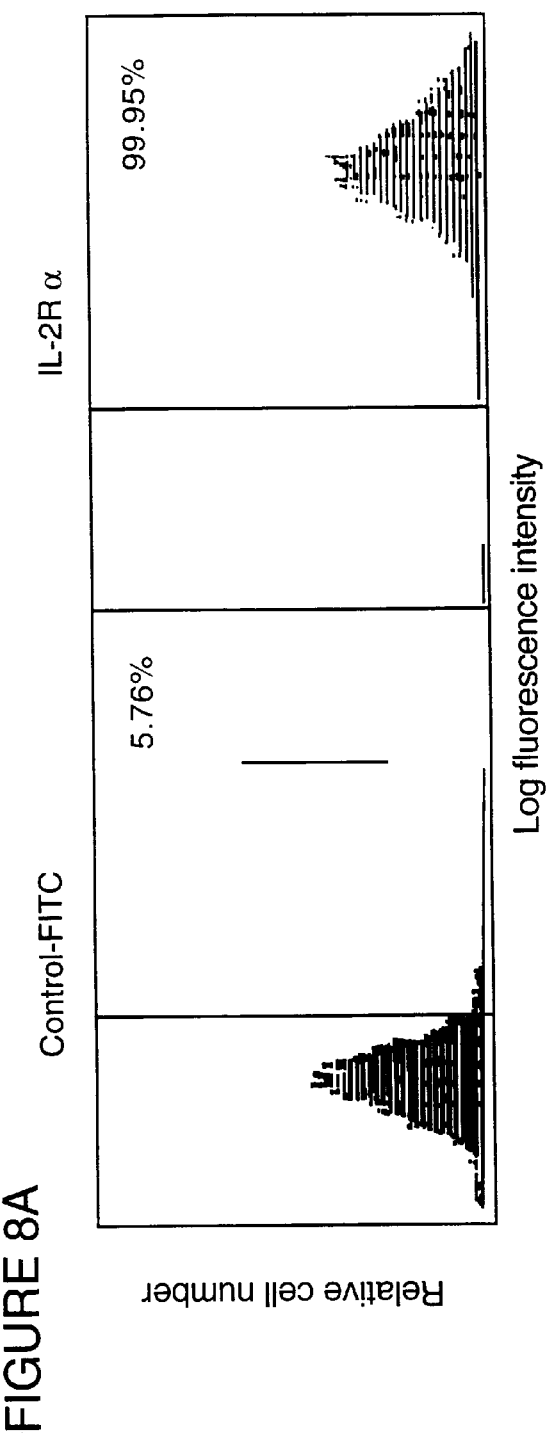

FIGS. 8A & B is a graph illustrating that IS-2.15 supernatant does not modify IL-2R$\alpha$ expression on HT-2 cells.

Figure 9:
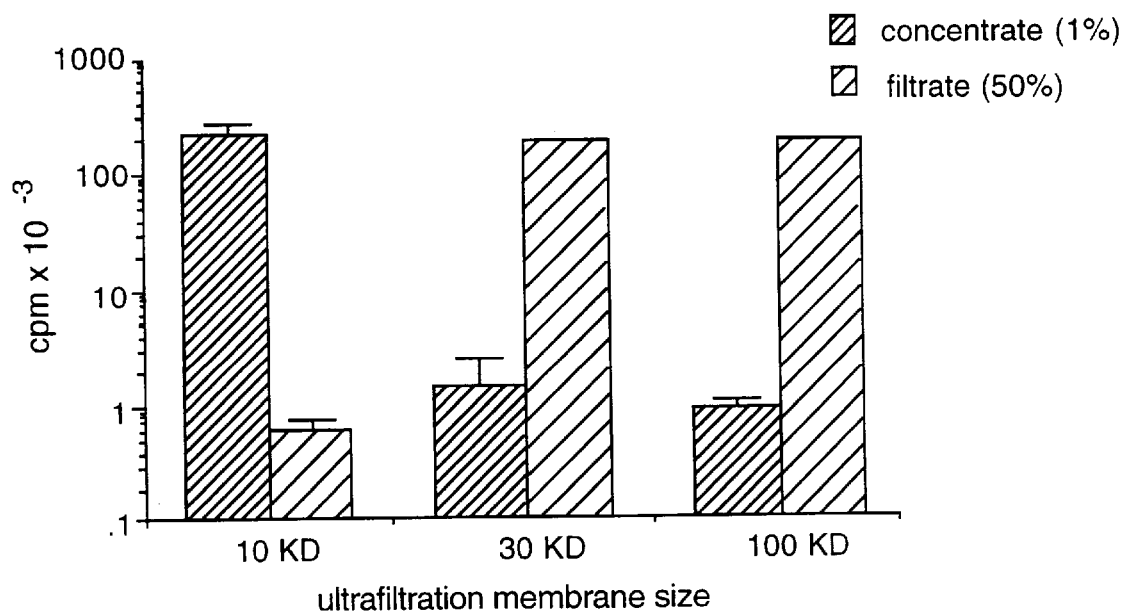

FIG. 9 is a graph illustrating that the molecular weight of IS-2.15 supernatant suppressor activity is between 10 and 30 kDa.

Figure 10:
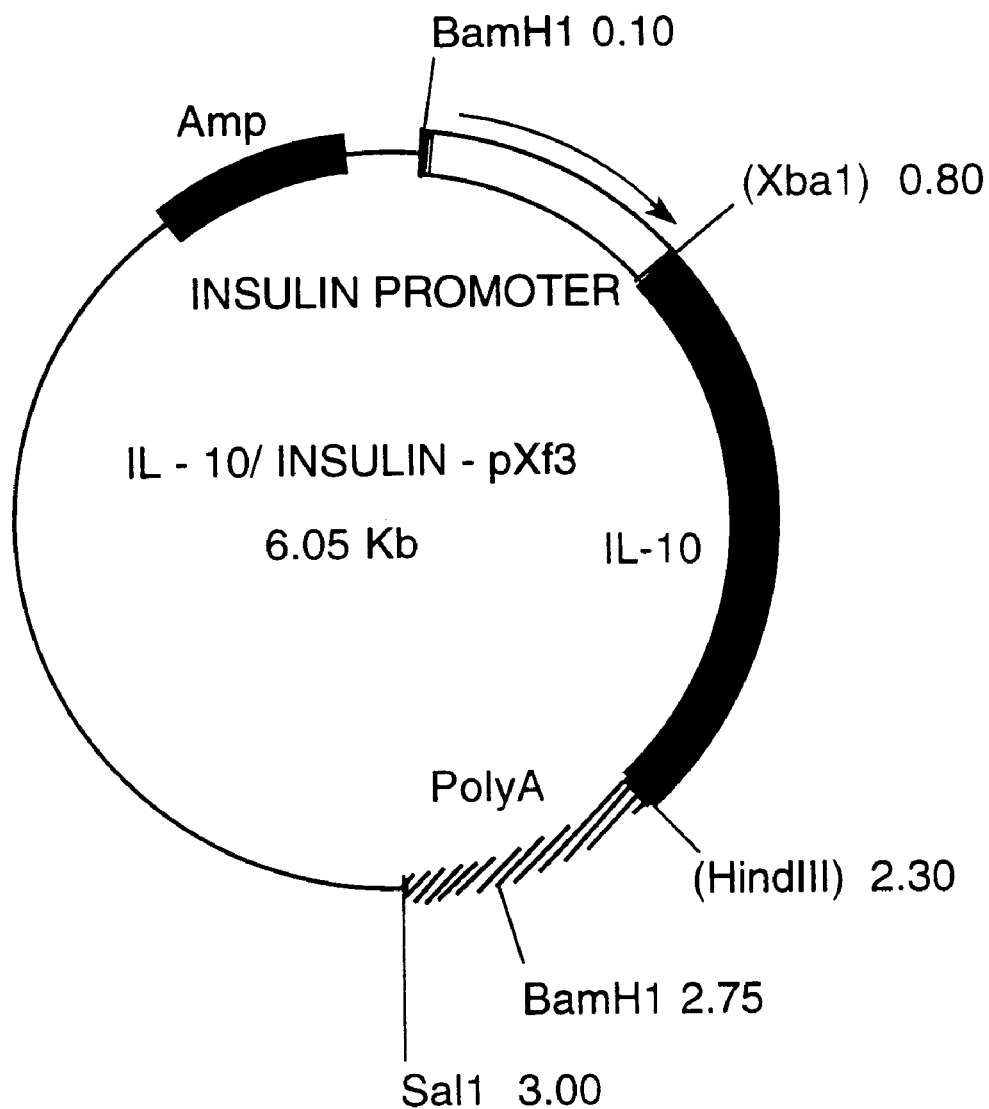

FIG. 10 is a diagram of plasmid, IL-10/INSULIN-pSf3. It is 6.05 kb in size. The IL-10 gene was cloned into the plasmid, pSf3, and it is under the transcriptional control of the insulin promoter.

Figure 11:
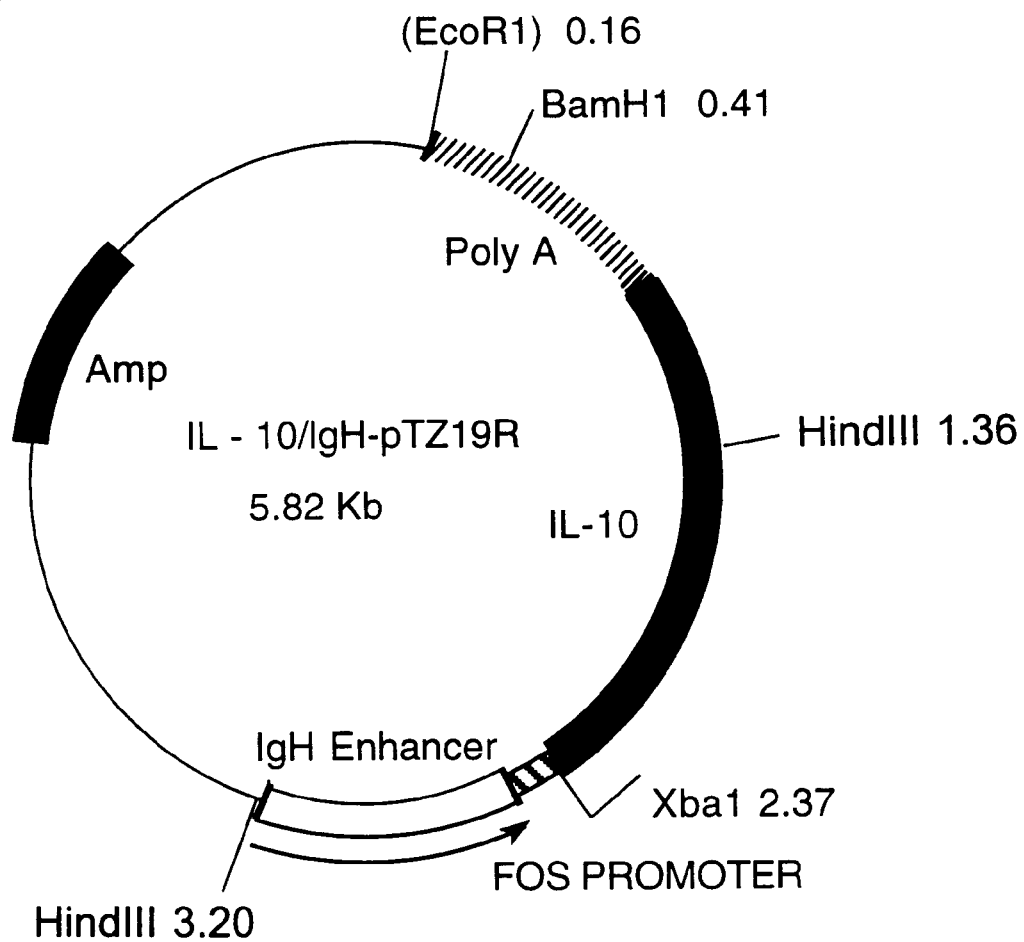

FIG. 11 is a diagram of plasmid, IL-10/IgH-pTZ19R. It is 5.82 kb in size. The IL-10 gene was cloned into the plasmid, pTZ19R, and it is transcribed under the control of the IgH enhancer/fos promoter.

Figure 12:
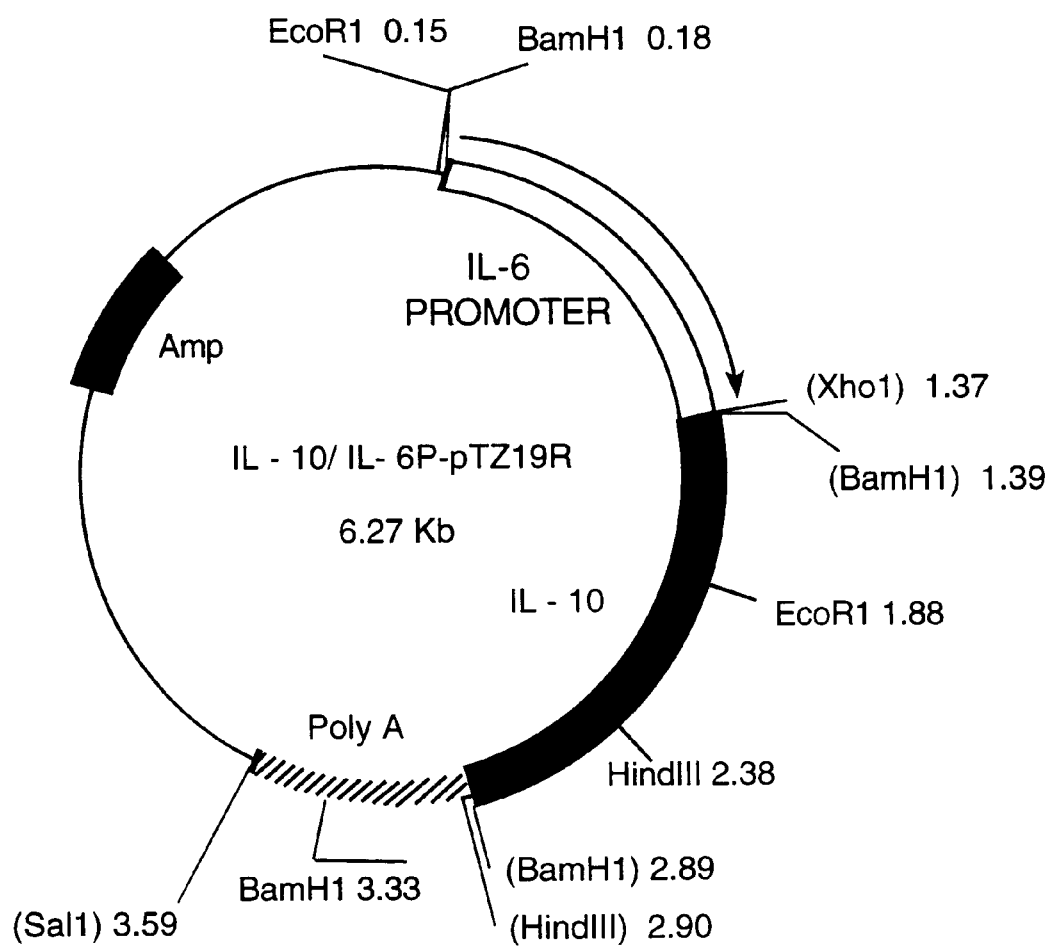

FIG. 12 is a diagram of plasmid, IL-10/IL-6P-pTZ19R. It is 6.27 kb in size. The IL-10 gene was cloned into the pTZ19R plasmid and it is transcribed under the control of the IL-6 promoter.

Figure 13:
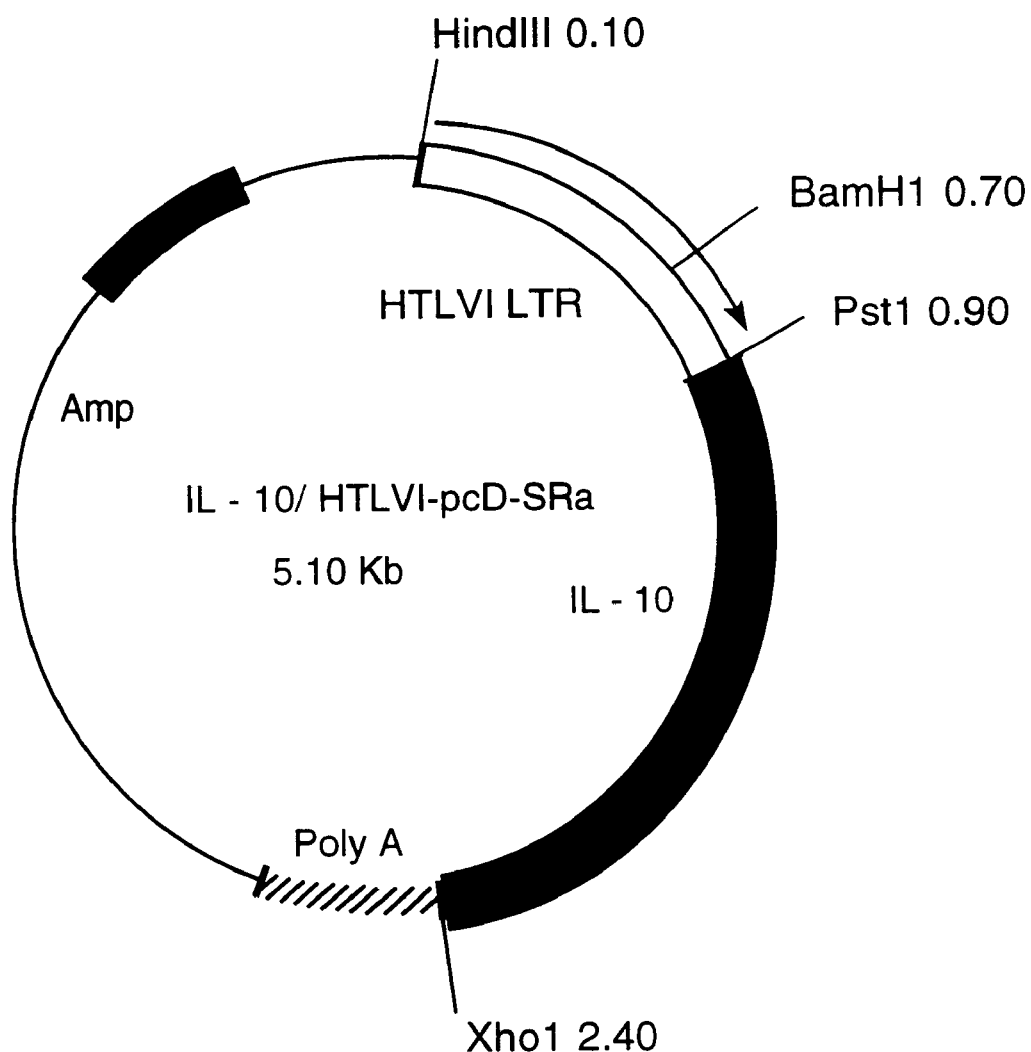

FIG. 13 is a diagram of plasmid, IL-10/HTLVI-pcD-SR$\alpha$. It is 5.10 kb in size. The IL-10 gene was cloned into the pcD-SR$\alpha$ plasmid and it is transcribed under the control of the HTLV1 LTR.

Figure 14:
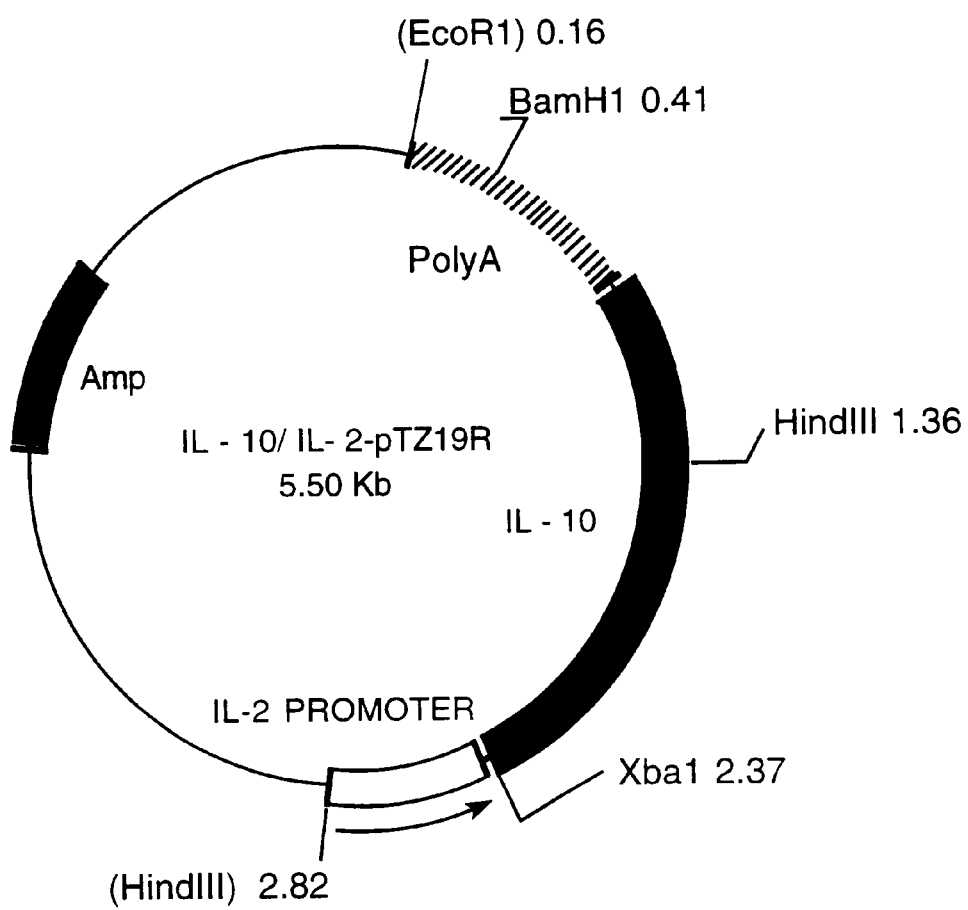
Figure 15A:
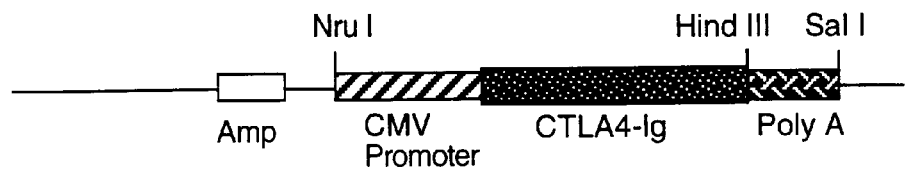
Figure 15B:
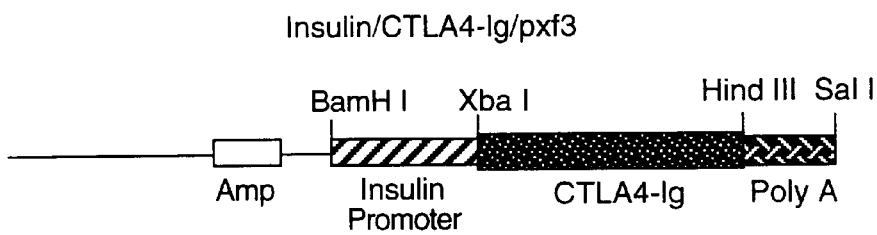
Figure 15C:
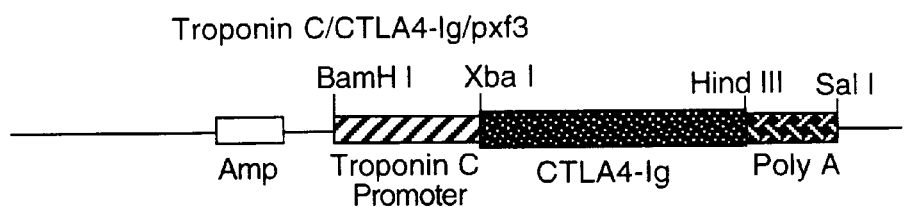
Figure 15D:
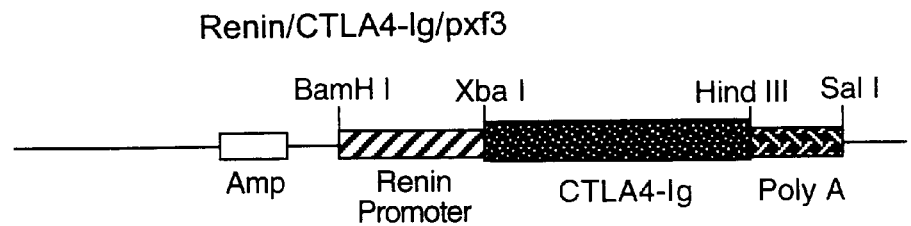
Figure 15E:
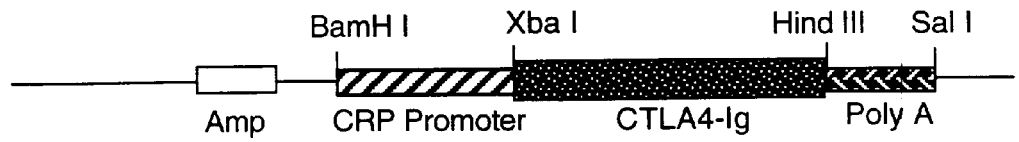
Figure 15F:
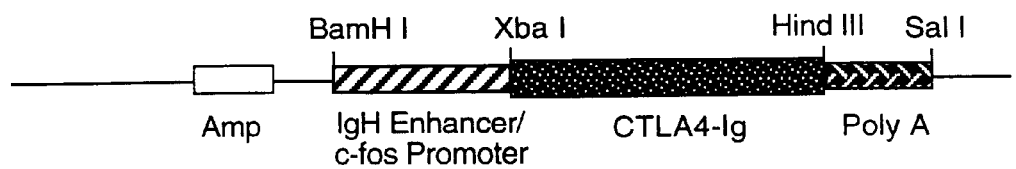
Figure 15G:
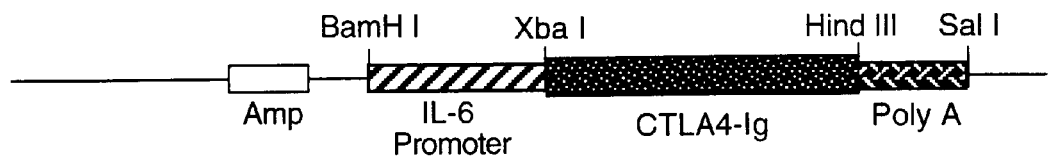
Figure 15H:
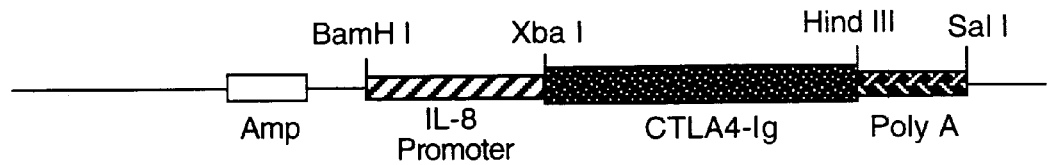
Figure 15I:
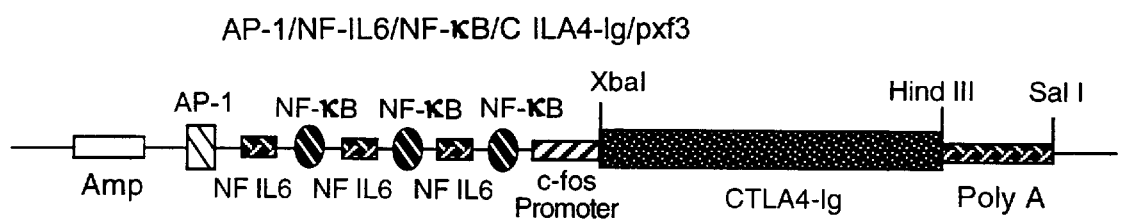
Figure 15J:
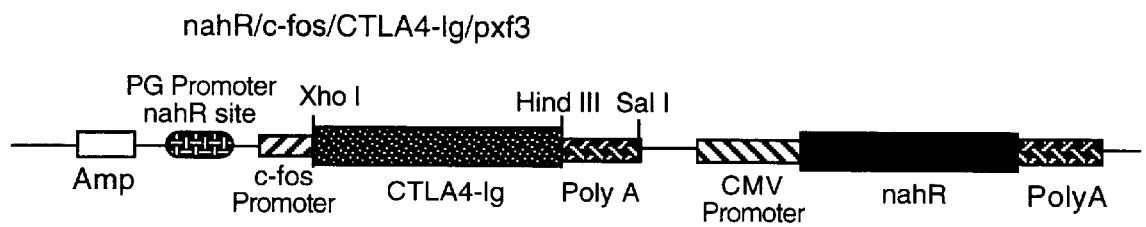
Figure 15K:
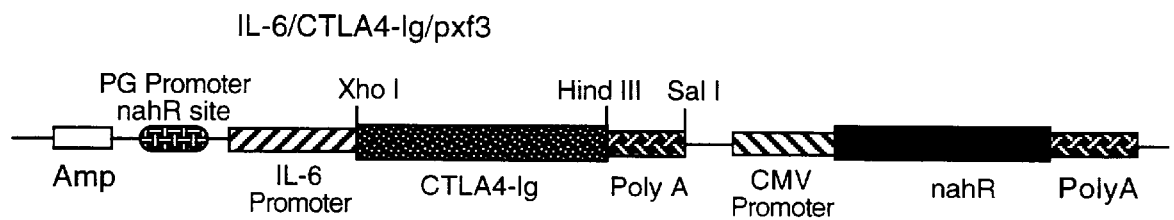

FIG. 14 is a diagram of plasmid, IL-10/IL-2-pTZ19R. It is 5.50 kb in size. The IL-10 gene was cloned into the pTZ19R plasmid and it is transcribed under the control of the IL-2 promoter.

FIG. 15 is a diagram of constructs expressing CTLA4-Ig under the control of various promoters.

The following will now be described in detail: I. Inhibition of rejection of transplanted tissue and prevention of tissue destruction due to autoimmune disease and II. Isolation and characterization of the novel suppressor factor.

I. Inhibition of Rejection of Transplanted Tissue and Prevention of Tissue Destruction Due to Autoimmune Disease There follows a detailed description of the methods by which rejection of organs and tissues, and prevention of tissue destruction due to autoimmune disease can be inhibited according to methods of the invention.

A central feature of the invention is the design of therapies which specifically suppress the local immune response at the site of potential rejection or autoimmune destruction of the tissue or organ. This strategy, which targets immunosuppression to the specific anatomical region where it is needed, represents an improvement over existing clinical therapies, all of which involve general suppression of the immune response. To utilize the methods for treatment of the varied conditions described herein modifications of the general technique may be employed.

The protein encoded by the DNA transfecting cells of the transplanted tissue can exert its immunosuppressive effects in any of several ways, for example: (1) the protein itself can exert a direct immunosuppressive effect; (2) the protein can be an enzyme which acts on a substrate to convert a polypeptide substrate into an active immunosuppressive compound; or (3) the protein can be an enzyme which is capable of activating a prodrug which, when activated, is an immunosuppressive compound.

In the aspect of the invention which features prevention of transplanted tissue or organ rejection, the recombinant gene is, preferably, introduced into the cells of the tissue/organ prior to transplantation of the tissue/organ into the mammal. This can be accomplished by ex vivo transfection of isolated cells of the tissue/organ, or by transfection of the tissue/organ itself. Introduction of the DNA can also be accomplished by transfection of the tissue/organ in vivo, for example, by introducing suitably prepared DNA directly into the tissue/organ of the mammal following transplantation. Another method for the introduction of DNA into an organ involves the generation of transgenic animals in which the appropriate genes are expressed in the organ to be transplanted.

In an alternative method, the transfected cells may be in the area surrounding the transplant, but not a part of the actual transplant. For example, cultured myoblasts or immortalized renal epithelial cells may be transplanted. The transfected cells may then be intermixed with islet allografts, or may be injected into or near organ allografts (i.e. under the renal capsule).

Following transplantation, the proteins are expressed and act to inhibit rejection of the transplanted tissue/organ.

In the aspect of the invention which features the treatment of autoimmune disease, the recombinant gene is introduced into the affected tissues or surrounding tissues, preferably prior to localized onset of the disease phenotype. For example, in patients suffering from systemic lupus erythematosus (SLE), the recombinant gene may be introduced into the kidney or cardiac muscle tissues. In prediabetic patients it is preferable to introduce the recombinant transgene into the β-cells of the pancreas. The preferred target tissues for treating rheumatoid arthritis patients are the synovial tissues of the joints, and the brain and myelin sheath are preferred targets in patients suffering from multiple sclerosis. As with therapies for transplantation, cells such as myoblasts and renal epithelia cells may be transplanted into the effected area after they are altered to express the transgene appropriately.

Construction of Recombinant Genes

Recombinant proteins capable of mediating inhibition of rejection of a transplanted tissue/organ by modulating the localized immune response include, but are not limited to, naturally occurring proteins such as IL-10, TGF-β and other IL-2 suppressor factors such as that produced by the T cell clone, IS-2.15 (described more fully below). In addition, DNA encoding non-naturally occurring polypeptides such as IL2Ig, CD2Ig, and CTLA-4 Ig fusion proteins may also be employed (see below). The genes encoding IL-10 and TGF-β have been cloned into plasmid vectors as described below. The expression of these genes can be driven by any one of a number of promoters which are described in Table 1 and Table 2.

TABLE 1

PROMOTER CONSTRUCTS

| PROMOTER TYPE | PROMOTER ELEMENT | REFERENCES |
|---|---|---|
| CONSTITUTIVE | β-actin | Liu et al., Mol. Cell Biol. 10:3432–40 (1990) |
| | tubulin | Angelichio et al., Nucleic Acids Res. 19:5037–43 (1991) |
| | CMV | see Invitrogen |
| | SV40 enhancer | see Pharmacia |
| | RSV-LTR | see Invitrogen |
| | Adenovirus enhancer | Inoue et al., Biochem Biophys Res Commun 173: 1311–6 (1990) |
| TISSUE-SPECIFIC LIVER | serum amyloid A | Li et al., Nucleic Acids Res 20:4765–72 (1992) |
| | phenylalanine hydroxylase | Wang et al., J Biol Chem 269:9137–46 (1994) |
| | IGFBP-1 | Babajko et al., PNAS 90: 272–6 (1993) |
| | apolipoprotein B | Brooks et al., Mol Cell Biol 14:2243–56 (1994) |
| | albumin | Pinkert et al., Genes Dev 1: 268–76 (1987) |
| | vitellogenin | Corthesy et al., Mol Endocrinol 5:159–69 (1991) |
| | angiotensinogen | Brasier et al., Embo J 9: 3933–44 (1990) |
| | haptoglobin | Yang et al., Genomics 18: 374–80 (1993) |
| | PEPCK | Short et al., Mol Cell Biol 12:1007–20 (1992) |
| | factor IX | Jallat et al., Embo J 9: 3295–301 (1990) |
| | transferrin | Idzerda et al., Mol Cell Biol 9:5154–62 (1989) |
| | β-fibrinogen | Dalmon et al., Mol Cell Biol 13:1183–93 (1993) |
| | kininogen | Chen et al., Mol Cell Biol 13:6766–77 (1993) |
| | CRP | Toniatti et al., Mol Biol Med 7:199–212 (1990) |
| KIDNEY | renin | Fukamizu et al., Biochem Biophys Res Commun 199: 183–90 (1994) |
| HEART | cardiac myosin light chain | Lee et al., J Biol Chem 267:15875–85 (1992) |
| | cardiac troponin C | Parmacek et al., Mol Cell Biol 12:1967–76 (1992) |
| | α-cardiac myosin heavy chain | Gulick et al., J Biol Chem 266:9180–5 (1991) |
| | MCK | Johnson et al., Mol Cell Biol 9:3393–9 (1989) |
| | troponin I atrial natriuretic factor | Rockman et al., PNAS 88: 8277–81 (1991) erratum 88(21):9907 |
| LUNG | pulmonary surfactant protein SP-C | Glasser et al., Am J Physiol L349–56 (1991) |
| PANCREAS/ISLET | insulin | Dandoy et al., Nucleic Acids Res 19:4925–30 (1991); and Selden et al., Nature 321:525–8 (1986) |
| | pancreatic amylase | Osborn et al., Mol Cell Biol 7:326–34 (1987) |

TABLE 1-continued

PROMOTER CONSTRUCTS

| PROMOTER TYPE | PROMOTER ELEMENT | REFERENCES |
|---|---|---|
| BRAIN/GLIA | GFAP | Brenner et al., J Neurosci 1030–7 (1994) |
| | JCV | Henson et al., J Biol Chem 269:1046–50 (1994) |
| | MBP | Miskimins et al., Brain Res Dev Brain Res 65:217–21 (1992) |
| | serotonin 2 receptor | Ding et al., Brain Res Mol Brain Res 20:181–91 (1993) |
| | myelin PO | Monuki et al., Mech Dev 42:15–32 (1993) |
| | myelin proteolipid protein | Berndt et al. J Biol Chem 267:14730–7 (1992) |
| INDUCIBLE | | |
| A) IMMUNE RESPONSE/NATURAL | IL-2 | Thompson et al., Mol Cell Biol 12:1043–53 (1992) |
| | IL-4 | Todd et al., J Exp Med 177: 1663–74 (1993) |
| | IL-6 | Libermann et al., Mol Cell Biol 10:2327–34 (1990); and Matsusaka et al., PNAS 90:10193–7 (1993) |
| | IL-8 | Matsusaka et al., PNAS 90:10193–7 (1993) |
| | IL-10 | Kim et al., J Immunol 148: 3618–23 (1992) |
| | TNF-α | Drouet et al., J Immunol 147:1694–700 (1991) |
| | IL-1 | Shirakawa et al., Mol Cell Biol 13:1332–44 (1993) |
| | MIP-1 | Grove et al., Mol Cell Biol 13:5276–89 (1993) |
| | IFN-γ | Penix et al., J Exp Med 178:1483–96 (1993) |
| | VCAM-1 | Iademarco et al., J Biol Chem 267:16323–9 (1992) |
| | ICAM-1 | Voraberger et al., J Immunol 147:2777–86 (1991) |
| | ELAM-1 | Whelan et al., Nucleic Acids Res 19:2645–53 (1991) |
| | tissue factor | Mackman et al., J Exp Med 174:1517–26 (1991) |
| | IFN-β | Visvanathan et al., Embo J 8:1129–38 (1989) |
| | c-jun | Muegge et al., PNAS 90: 7054–8 (1993) |
| | junB | Nakajima et al., Mol Cell Biol 13:3017–41 (1993) |
| | c-fos | Morgan et al., Cell Prolif 25:205–15 (1992) |
| | iNOS | Xie et al., J Exp Med 177: 1779–84 (1993) |
| | G-CSF | Shannon et al., Growth Factors 7:181–93 (1992) |
| | GM-CSF | Miyatake et al., Mol Cell Biol 11:5894–901 (1991) |
| B) IMMUNE RESPONSE/SYNTHETIC multiple copies of binding sites | NF-KB | Lenardo et al., Cell 58: 227–9 (1989) |
| | NF-IL6 | Akira et al., Embo J 9: 1897–906 (1990) |
| | IL6-response element | Wegenka et al., Mol Cell Biol 13:276–88 (1993) |
| | CRE | Brindle et al., Curr Opin Genet Dev 2:199–204 (1992) |
| | AP-1 | Auwerx et al., Oncogene 7: 2271–80 (1992) |
| | p91/stat combinations of multiple NF-KB and NF-IL6 or combinations with the other elements | Larner et al., Science 261: 1730–3 (1993) |
| C) EXOGENOUS/NON-MAMMALIAN | IPTG inducible/lac repressor/ operon system | see Stratagene LacSwitch ™, La Jolla, CA |
| | ecdysone-inducible promoter/ ecdysone receptor | Burtis et al., Cell 61:85–99 (1990) |
| | Na-salicylate-inducible promoter | Yen, J Bacteriol 173: 5328–35 (1991) |
| | PG/regulator nahR | |
| | nalidixic acid inducible recA promoter | Rangwala et al., Bio-technology 9:477–9 (1993) |

TABLE 2

PREFERRED THERAPEUTIC PROMOTER COMBINATIONS

GRAFT REJECTION

| TRANSPLANT ORGAN OR TISSUE | PROMOTER CONSTRUCTS CONSTITUTIVE | TISSUE-SPECIFIC | IMMUNE RESPONSE INDUCIBLE | SYNTHETIC INDUCIBLE | ORALLY INDUCIBLE | COMBINATIONS |
|---|---|---|---|---|---|---|
| Heart | CMV | cardiac troponin C atrial natriuretic factor | interleukin-6 interleukin-8 | combination of multiple copies of NF- | Na-salicylate-inducible promoter | IL-6 + additional copies of NF-κB or |

TABLE 2-continued

| | | | | | | | |
|---|---|---|---|---|---|---|---|
| | | | | κB, NF-IL6 and AP-1 | PG/regulator nahR | NF-IL6 + Na-salicylate-inducible promoter PG/regulator nahR | |
| Lung | CMV | pulmonary surfactant protein SP-C | interleukin-6 interleukin-8 | combination of multiple copies of NF-κB, NF-IL6 and AP-1 | Na-salicylate-inducible promoter PG/regulator nahR | IL-6 + additional copies of NF-κB or NF-IL6 + Na-salicylate-inducible promoter PG/regulator nahR | |
| Kidney | CMV | renin | interleukin-6 interleukin-8 | combination of multiple copies of NF-κB, NF-IL6 and AP-1 | Na-salicylate-inducible promoter PG/regulator nahR | IL-6 + additional copies of NF-κB or NF-IL6 + Na-salicylate-inducible promoter PG/regulator nahR | |
| Liver | CMV | CRP β-fibrinogen | interleukin-6 interleukin-8 | combination of multiple copies of NF-κB, NF-IL6 and AP-1 | Na-salicylate-inducible promoter PG/regulator nahR | IL-6 + additional copies of NF-κB or NF-IL6 + Na-salicylate-inducible promoter PG/regulator nahR | |
| Bone marrow | CMV | immunoglobulin heavy chain enhancer | interleukin-6 interleukin-8 | combination of multiple copies of NF-κB, NF-IL6 and AP-1 | Na-salicylate-inducible promoter PG/regulator nahR | IL-6 + additional copies of NF-κB or NF-IL6 + Na-salicylate-inducible promoter PG/regulator nahR | |
| Pancreas/islet | CMV | insulin | interleukin-6 interleukin-8 | combination of multiple copies of NF-κB, NF-IL6 and AP-1 | Na-salicylate-inducible promoter PG/regulator nahR | IL-6 + additional copies of NF-κB or NF-IL6 + Na-salicylate-inducible promoter PG/regulator nahR | |

AUTOIMMUNITY

| DISEASE | PROMOTER CONSTRUCTS CONSTITUTIVE | TISSUE-SPECIFIC | IMMUNE RESPONSE INDUCIBLE | SYNTHETIC INDUCIBLE | ORALLY INDUCIBLE | COMBINATIONS | TARGET |
|---|---|---|---|---|---|---|---|
| Rheumatoid Arthritis | CMV | | interleukin-6 interleukin-8 | combination of multiple copies of NF-κB, NF-IL6 and AP-1 | Na-salicylate-inducible promoter PG/regulator nahR | IL-6 + additional copies of NF-κB or NF-IL6 + Na-salicylate-inducible promoter PG/regulator nahR | synovium |
| Multiple Sclerosis | CMV | myelin basic protein JCV glial fibrillary acidic protein | interleukin-6 interleukin-8 | combination of multiple copies of NF-κB, NF-IL6 and AP-1 | Na-salicylate-inducible promoter PG/regulator nahR | IL-6 + additional copies of NF-κB or NF-IL6 + Na-salicylate-inducible promoter PG/regulator nahR | brain |
| Systemic Lupus erythematosis | CMV | renin cardiac troponin C | interleukin-6 interleukin-8 | combination of multiple copies of NF-κB, NF-IL6 and AP-1 | Na-salicylate-inducible promoter PG/regulator nahR | IL-6 + additional copies of NF-κB or NF-IL6 + Na-salicylate-inducible promoter PG/regulator nahR | kidnet, heart |
| Diabetes | CMV | insulin | interleukin-6 interleukin-8 | combination of multiple copies of NF-κB, NF-IL6 and AP-1 | Na-salicylate-inducible promoter PG/regulator nahR | IL-6 + additional copies of NF-κB or NF-IL6 + Na-salicylate-inducible promoter PG/regulator nahR | pancreas |

These promoters were selected because they either control expression of the proteins in an inducible manner, are tissue specific, or cause the protein to be expressed constitutively in the localized cells into which the DNA is transfected. The recombinant technology required to clone and express such genes is standard in the art and is described in detail, for example, in Sambrook et al. (Molecular Cloning. A Laboratory Manual. Cold Spring Harbor Press, Cold Spring Harbor, N.Y., 1989).
Promoters Examples of promoters conferring constitutive, immunoresponsive, tissue specific or inducible expression on genes include, but are not limited to, the promoters provided in Table 1, Table 2 and FIGS. 10–15.
Regulatory elements of the IL-6 promoter The following is a detailed discussion of the IL-6 regulatory elements. Equivalent information is widely available for other promoters described herein.

Interleukin-6 (IL-6) is a cytokine released by a variety of cells including macrophages, endothelial cells, fibroblasts, T cells, glial cells and B cells in response to a variety of stimuli (Kishimoto, 1989 Blood, 74:1–10). In particular IL-6 gene expression is stimulated by all substances that trigger an immune response and inflammation, the same agents released during acute rejection (Kishimoto, 1989 Blood, 74:1–10). The IL-6 promoter is composed of a variety of overlapping regulatory elements (Kishimoto, 1989 Blood, 74:1–10). The IL-6 promoter has been cloned and inserted upstream of the chloramphenicol acetyltransferase gene. A 1.2 kb fragment of the 5' flanking region of the IL-6 gene (Ray, et al., 1988 Proc. Natl. Acad. Sci. USA, 85:6701–6705; Yasukawa, et al., 1987 Embo J., 6:2939–2945) contains all the necessary elements for induction of the IL- 6 gene. Analysis of the promoter region of the IL-6 gene revealed the presence of a putative binding site for the transcription factor NF-kB (Libermann, et al., 1990 Mol. Cell. Biol., 10:2327–2334).

Putative regulatory elements of the IL-6 promoter

To characterize the functional role of the putative NF-KB binding site, mutations were introduced into the IL-6kB site using synthetic oligonucleotides and the gapped/heteroduplex method (Stewart, et al., 1988 Biotechniques, 6:511–518) and examined for their effects on inducibility of the IL-6 gene. Enhancer activity was measured as the ability of the different enhancer constructs to induce transcription of the chloramphenicol acetyltransferase (CAT) gene after transient expression in a variety of cell types (Libermann, et al., 1990 Mol. Cell. Biol., 10:3155–3162; Gorman, et al., 1982 Mol. Cell. Biol., 2:1044–1051; Gilman, et al., 1986 Mol. Cell. Biol., 6:4305–4316). Transfections of U-937 monocytic cells, Jurkat T cells and HeLa cells were carried out using the DEAE-dextran method (Pierce, et al., 1988 Proc. Natl. Acad. Sci. USA, 85:1482–1486). The apparent NF-Kb binding site is an indispensable component of the IL-6 control region. The IL-6 promoter Kb site binds NF-Kb and its alteration abolishes inducibility of chimeric genes driven by the IL-6 promoter (FIG. 4) (Libermann, et al., 1990 Mol. Cell. Biol., 10:2327–2334). It appears that the ability of various agents including LPS, PMA, TNF-α and dsRNA to induce IL-6 expression is a consequence of their ability to activate NF-Kb. A second enhancer element, NF-IL-6, was also shown to respond to IL-1, IL-6, TNFα, and LPS (Isshiki, et al., 1990 Mol. Cell. Biol., 10:2757–2764) and recent evidence suggests that NF-kB interacts cooperatively with the NF-IL-6 factor (Mukaida, et al., 1990 J. Biol. Chem., 265:21128–21133). Mutations in either elements will abolish inducibility. Ray et al. identified an additional element, MRE, that overlaps with a potential cAMP responsive element (CRE) (Ray et al., 1989 Mol. Cell. Biol., 9:5537–5547). The MRE is apparently induced by phorbol ester, IL-1, TNF-α and forskolin (Ray et al., 1989 Mol. Cell. Biol., 9:5537–5547). In addition, two putative glucocorticoid response elements and an AP-1 binding site have been identified in the IL-6 promoter (Kishimoto, 1989 Blood, 74:1–10). Potential binding sites for HLH and ets related transcription factors are also present, as well as a putative binding site for factors of the GATA gene family (Martin, et al., 1990 Nature, 344:444–447). The IL-6 promoter can be used as an inducible promoter for IL-10 and TGF-β expression (see Dendorfer et al., Mol. Cell. Biol., 14:4443–4454 (1994), incorporated herein by reference).

Additional Promoters

Publicly available promoters that are inducible by factors involved in the immune response include NFκB and NF-IL-6, both of which are induced by IL-1 and other immune response mediators; interferon response element, which is induced by γ-interferon; IL-6 response element, which is induced by IL-6; CRE, which is induced by prostaglandins. Promoters that are inducible by exogenous factors include the glucocorticoid response element, which is induced by glucocorticoids; retinoic acid response element, which is induced by retinoic acid; NF-κ and NF-IL-6, which are induced by inflammatory agents; Verapamil response element and OS-1 response element, which are induced by verapamil and OS-1; glucose response element, which is induced by glucose; Mouse Mammary Tumor Virus LTR, which is induced by dexamethasone.

Examples of promoters that confer constitutive expression include, but are not limited to, the following: The human T cell leukemia virus type 1 long terminal repeat; the Rous sarcoma virus long terminal repeat; the Moloney murine leukemia virus long terminal repeat; the simian virus 40 early enhancer/promoter; the cytomegalovirus immediate early promoter; the β-actin promoter; the islet cell insulin promoter; the B cell immunoglobulin enhancer/promoter; the T cell receptor enhancer promoter that is T cell specific, such as the HTLV-1 promoter, or an endothelial cell specific promoter.

Plasmids or other vectors encoding most of these promoters are commercially available. Where this is not the case, the promoters can be isolated and cloned into appropriate plasmids or vectors by conventional recombinant techniques following the directions provided in Sambrook et al. (Supra).

Genetic Constructs

Examples of genetic constructs which have been made are include IL-10 cDNA driven by the insulin promoter (FIG. 10); IL-10 cDNA driven by the immunoglobulin heavy chain promoter (FIG. 11); IL-10 cDNA driven by the IL-6 promoter (FIG. 12) ;IL-10 cDNA under the control of the SRα promoter (FIG. 13) (Takebe, Y. et al. 1988, Mol. Cell Biol., 8:466), and; IL-10 cDNA driven by the IL-2 promoter (FIG. 14).

Similarly, the human TGF-β1 cDNA (Derynck, et al., 1985 Nature, 316:8) and other genes for immunosuppressive proteins can be inserted into such vectors. For inducible expression, cDNAS can be cloned directly downstream of the IL-6 (Libermann, et al., 1990 Mol. Cell. Biol., 10:2327–2334) or the IL-2 (Hoyos, et al., 1989 Science, 244:457–460; Fraser, et al., 1991 Science, 251:313–316) promoters. Both promoters are highly inducible by several agents, particularly substances released from activated macrophages during immune response (Kishimoto, 1989 Blood, 74:1–10; Crabtree, 1982, Science, 243:355–361).

To evaluate expression of IL-10 or TGF-β by the transfected cells, several different assays, such as the IL-10 ELISA assay, described in Current Protocols in Immunology (Mosmann, 1991 In: Current Protocols in Immunology; 1:6.14.1–6.14.8) herein incorporated by reference, can be used. IL-10 activity is determined by the ability of IL-10 to inhibit cytokine production by activated macrophages and this can be measured in a bioassay (Fiorentino, D. F. 1991, J. Immunol., 147:3815), herein incorporated by reference). TGF-β expression can be measured by either the thymocyte proliferation assay in the presence or absence of neutralizing anti-TGF-β1 antibodies (Genzyme Corporation, Cambridge, Mass.) or by a radioreceptor assay using A549 lung carcinoma cells (deposited with the ATCC) as described (Mosmann, 1991 In: Current Protocols in Immunology; 1:6.14.1–6.14.8).

Activation of a pro-drug

A gene encoding an enzyme that activates an immunosuppressive drug can be cloned and expressed in T-cells or in a graft. Expression of a gene such as cyclosporine synthetase (Lawen, A. 1990, J. Biol. Chem., 265:11355) by the graft would activate the drug, e.g., a cyclosporine precursor, and create an environment of local immunosuppression, thus allowing improved survival of the grafted tissue or organ.

Another immunosuppressive agent that must be metabolized before becoming active is cyclophosphamide. Cyclophosphamide metabolism normally takes place in liver microsomes. The genes encoding the activating enzymes may be cloned and expressed in T cells or engrafted organs, resulting in local activation of the drug.
Enzymes that act to produce a compound capable of inhibiting rejection of a tissue or organ.

Molecules that are the target for preformed antibodies, which present the biggest barrier for xenotransplants, are largely molecules that are heavily glycosylated (Geller et al, 1992, Transplant. Proc., 24:592). The glycosylation sites appear to be targets for these antibodies. Antigenic determinants are frequently located on N-linked substitutions. To eliminate the targets for such xenoreactive natural antibodies, a glycosidase can be expressed in the transplanted organ.

Immunosuppressive Fusion Proteins

DNA encoding immunosuppressive fusion proteins may also be employed to prevent graft rejection and autoimmune mediated tissue destruction. Such fusion genes may encode immunosuppressive amino acid sequences from for example, IL-2, CD2 or CTLA-4 linked to the Fc portion of the Ig heavy chains. The Fc portion of the Ig heavy chains is known to stabilize soluble proteins. The IL-2 Ig fusion encoded by these constructs binds to activated lymphocytes causing direct killing through the Fc of the IgG component. The CD2 and CTLA4 Fg fusions possess an Fc portion which does not activate complement or bind with FcR$^+$ phagocytes, but which does confer an extended half life. Thus, the CD2 and CTLA4 fusion molecules serve to block costimulatory T-cell activation signals. CTLA4 Ig proteins and DNA encoding the same are described in Linsley et al., *J. Exp. Med.,* 174:561–569 (1991); Lenschow et al., *Science,* 257:789–792 (1992); Linsley et al., *Science,* 257:792–795 (1992); and Turka et al., *PNAS,* 89:11102–11105 (1989) and DNA encoding the same are described in Steurer et al., *J. Amer. Soc. Nephrol.,* 4:919 (1993) and Kato et al., *J. Exp. Med.,* 176:1241–1249 (1992). IL-2 immunoligands and DNA encoding the same are described in Landolfi, *J. Immunol.,* 146:915–919 (1991), Vie et al., *PNAS,* 89:11337–11341 (1992), and Steele et al., *J. Amer. Soc. Nephrol.,* 4:636. All these references are incorporated herein.

Introduction of Recombinant Genes into Cells of Tissues

A number of methods can be employed for the introduction of recombinant genes into cells of a tissue or organ. In addition to those examples provided below, Table 3 provides further examples of methods which may be used to deliver DNA both in vitro and in vitro.

TABLE 3

EXAMPLES OF GENE TRANSFER PROTOCOLS*

| TARGET TISSUE | METHOD | REFERENCES |
| --- | --- | --- |
| A. General | Liposome | Nabel et al., PNAS USA, 90: 11307–11 (1993) |
| | | Nabel et al., Hum. Gene Ther., 3:649–56 (1992) |
| | | Zhu et al., Science, 261:209–11 (1993) |
| | Particle | Cheng et al., PNAS USA, 90: |

TABLE 3-continued

EXAMPLES OF GENE TRANSFER PROTOCOLS*

| TARGET TISSUE | METHOD | REFERENCES |
| --- | --- | --- |
| | Bombardment | 4455–9 (1993) |
| | Microcapsules | Chang et al., Hum Gene Ther., 4:433–40 (1993) |
| B. Muscle - generally | Retroviral | Dai et al., PNAS USA, 89: 10892–5 (1992) |
| | Cell transplantation | Gussoni et al., Nature, 356: 435–8 (1992) |
| | Adenoviral | Ragot et al., Nature, 361: 647–50 (1993) |
| | Liposome | Nabel et al., J. Clin. Invest., 91:1822–9 (1993) |
| | | Nabel et al., PNAS USA, 89: 5157–61 (1992) |
| C. Cardiac Muscle | In Vivo | Kass-Eisler et al., PNAS USA, 90:11498–502 (1993) |
| | In Vitro | Kass-Eisler et al., PNAS USA, 90:11498–502 (1993) |
| | Adenovirus | Kass-Eisler et al., PNAS USA, 90:11498–502 (1993) |
| D. Liver | Retroviral | Kay et al., Hum. Gene Ther., 3: 641–7 (1992) |
| | | Rettinger et al., PNAS USA, 91:1460–4 (1994) |
| | | Cardoso et al., Hum. Gene Ther., 4:411–8 (1993) |
| | Adenoviral Vector | Kay et al., PNAS USA, 91: 2353–7 (1994) |
| E. CNS - generally | Herpes Virus | Andersen et al., Cell Mol. Neurobiol, 13:503–15 (1993) |
| | Liposomes | Jiao et al., Exp. Neurol., 115: 400–13 (1992) |
| F. Neurons & Ganglia | Adenoviral | La Salle et al., Science, 259: 988–90 (1993) |
| G. Glial Cells | Glioma | Yamada et al., Jpn J Cancer Res., 83:1244–7 (1992) |
| | Retroviral | Yamada et al., Jpn J Cancer Res., 83:1244–7 (1992) |
| H. Lung | Adenovirus | Flotte et al., PNAS USA, 90: 10613–7 (1993) |

Transfection of Dispersed Cells from a Tissue or Organ

Transfection of dispersed cells from a tissue/organ can be accomplished by any number of known methods, including calcium phosphate precipitation, DEAE dextran, electroporation, and liposome mediated transfection. The method to be used for any given population of cells will depend upon the cell type that is being transfected and their sensitivity to the components of the transfection mixture. Each of these methods is well known to those skilled in the art, and are described in detail.

Viral Delivery

Retroviral vectors, or other viral vectors, such as adenoviral vectors, with the appropriate tropisms for cells useful for therapeutic delivery, may be used as a gene transfer delivery system for the methods of the invention. Numerous vectors useful for this purpose are generally known have been described (Miller, *Human Gene Therapy,* pp. 15–14 (1990); Friedman, *Science,* 244:1275–1281 (1989); Eglitis and Anderson, *BioTechniques,* 6:608–614 (1988); Tolstoshev and Anderson, *Current Opinion in Biotechnology,* 1:55–61 (1990); Sharp, *The Lancet,* 337:1277–1278 (1991); Cornetta et al., *Nucleic Acid Research and Molecular Biology,* 36:311–322 (1987); Anderson, *Science,* 226:401–409 (1984); Moen, *Blood Cells,* 17:407–416 (1991); and Miller and Rosman, *Biotechniques,* 7:980–990 (1989)). Retroviral vectors are particularly well developed and have been used in a clinical setting (Rosenberg, et al., *N. Engl. J. Med.,* 323:370 (1990)).

The retroviral constructs, packaging cell lines and delivery systems which may be useful for this purpose include, but are not limited to, one, or a combination of, the following: Moloney murine leukemia viral vector types; self inactivating vectors; double copy vectors; selection marker vectors; and suicide mechanism vectors. The Moloney murine leukemia retroviral system of IL-10 delivery is particularly useful since it targets delivery of the IL-10 protein to the hematopoietic cells which may be used for autologous of non-autologous therapy.

Non viral methods for delivery

Nucleic acid encoding the immunosuppressant polypeptides of the invention under the regulation of the appropriate promotor, and including the appropriate sequences required for insertion into genomic DNA of the patient, or autonomous replication, may be administered to the patient using the following gene transfer techniques: microinjection (Wolff et al., Science, 247:1465 (1990)); calcium phosphate transfer (Graham and Van der Eb, Virology, 52:456 (1973); Wigler et al., Cell, 14:725 (1978); Felgner et al., Proc. Natl. Acad. Sci. USA, 84:7413 (1987)); lipofection (Felgner et al., Proc. Natl. Acad. Sci. USA, 84:7413 (1987); Ono et al., Neuroscience Lett., 117:259 (1990); Brigham et al., Am. J. Med. Sci., 298:278 (1989); Staubinger and Papahadjopoulos, Meth. Enz., 101:512 (1983)); asialorosonucoid-polylysine conjugation (Wu and Wu, J. Biol. Chem., 263;14621 (1988); Wu et al., J. Biol. Chem., 264:16985 (1989)); and electroporation (Neumann et al., EMBO J., 7:841 (1980)). These references are hereby incorporated by reference, as are the additional reference.

Transfection of Whole Tissues or Organ

Tissue or organs, such as pancreatic islets, can be transfected using either electroporation (BioRad) as described by Welsh et al 1990 Proc. Natl. Acad. Sci USA. 87:5807–5811), lipofectin reagent (GIBCO-BRL), pH-sensitive liposomes as described by Welsh et al. (Welsh, et al., 1990 Biomed. Biochim. Acta, 49:1157–1164) or microparticle bombardment with the biolistic PDS-1000/He system (BioRad) (Yang, et al., 1990 Proc. Natl. Acad. Sci. USA, 87:9568–9572).

Transgenic Organs

Xenotransplantation of organs across species barriers has been proposed as a source of donor organs (Auchincloss, 1990 Transplant Rev., 4:14). In particular, experiments with pigs as xenograft donors for human patients are in progress (Gustafsson, et al., 1990 J. Immunol., 145:1946–1951). To prevent xenograft rejection, IL-10, TGF-β, or another protein with immunosuppressive activity can be expressed in the transgenic organ in either a tissue-specific or inducer-specific manner. In order to express IL-10 and/or TGF-β in either pancreatic islets or T cells of transgenic animals, the expression vector constructs described above can be used. For example, the HTLV I LTR driven IL-10 and TGF-β constructs can be used for T cell-specific expression, and the insulin promoter-driven IL-10 and TGF-β constructs can be used for pancreatic islet cell-specific expression.

For production of transgenic animals, expression vector constructs will be linearized and injected into oocytes according to standard protocols (Sarvetnick, et al., 1988 Cell, 52:773–782). Expression of the transgenes can be evaluated by sacrificing a second generation animal and isolating mRNA from different organs and from multiple hematopoietic cell types. Since constitutive expression of such genes in transgenic animals might lead to severe developmental defects or other pathological changes, the transgenic animals preferably contain genes of interest under the transcriptional control of inducible promoters as described above, such as the IL-6 promoter. IL-6 promoter driven constructs should be inducible in a variety of different cell types including endothelial cells, T cells, macrophages, fibroblasts, stromal cells, and mesangial cells (Kishimoto, 1989 Blood, 74:1–10).

Evaluation of Constructs

DNA constructs employed in the invention may be tested in vitro for their general immunosuppressive effect in vitro using the MCR assay (Coligan et al., Current Protocols in Immunology (1992) Wiley & Sons, Eds.). Those constructs which confer a 20% or greater decrease in proliferation relative to the control are useful in the methods of the invention.

Constructs may also be readily tested in vivo using the mouse islet transplant assay (see below) or other transplant and autoimmune modes readily available to those in the field. Promoters which may be used for the expression of the immunosuppressive proteins or glycosidases of the invention are shown in TABLE 1. Preferred promotor-gene combinations for the treatment of a graft rejection of various tissues are shown in TABLE 2, top and preferred promoter-gene constructs for the treatment of specific autoimmune diseases are shown in TABLE 2, bottom.

The methods of the invention may be used alone for the treatment of autoimmune disease or for the prevention of graft rejection or they may be used in combination with other known local or general immunosuppressive therapies.

Constructs of the invention which are immunosuppressive, as used herein, are those constructs which prolong engraftment beyond the 50% rejection period for the control animal similarly treated, but lacking the transgene. For example, constructs which include non-specific, constitutative, immune-responsive, inducible promoters, or β-cell specific promoters may be tested in the pancreatic islet cell transplant model described herein. Tissue specific expression may be listed in the appropriate cell type, or in transgenic mice, as discussed above. Constructs for use in the treatment of autoimmune disease may be evaluated by examination of tissue injury in the appropriate model. For example, mice with the epr gene, NOD mice and EAE mice may be utilized. In epr mice tissue injury in the kidney may be evaluated by immunopathologic techniques. For example, MRL-Lpr mice receiving epithelial cells which produce GM-CSF under the renal capsule may be compared to genetically identical mice receiving epithelical cells not containing the GMZSF encoding transgene. In such a test, those constructs which confer increased tissue survival relative tot he untreated control are useful in the methods described herein. Useful constructs are also those which provide a mixed lymphocyte reaction (MLR) by decreasing proliferation by 20%, more preferably by 40% and most preferably by 60% relative to control cells not expressing the transgene. This assay may be done as described in Current Protocols in Immunology (1992, Wiley & Sons, Eds., Coligan et al.).

A. Novel Suppressor Factor

There follows a detailed description of the transplant model in which the immunosuppressive effects of the suppressor factor of the invention were observed, followed by a description of the cells from which the factor was isolated, the procedure used for isolation, and the experiments in which immunosuppression was observed.

Use

Uses of the suppressor factor protein of the invention are based on its unique properties, in particular, its ability to block IL-2 stimulated T-cell proliferation without being cytotoxic or inhibiting the expression of IL-2 or IL-2 receptor. Uses fall into two main categories: diagnosis and therapy.

A nucleic acid encoding the suppressor factor of the invention can be used therapeutically to alter the effects of IL-2 on IL-2R bearing cells, or of IL-4 on IL-4R bearing cells. Four examples of how this method could be used include, but are not limited to, the following. 1) Cells that are targets of autoreactive IL-2R- or IL-4R-bearing cells can be transfected with a nucleic acid encoding the suppressor factor. The cell expresses and secretes the suppressor factor, which causes an alteration of the IL-2 effect, such that IL-2 dependent proliferation of autoreactive T-cells proximal to the cell are subject to inhibition by the suppressor factor. 2) Cells that are in close proximity to cells, e.g., autoreactive T-cells, as they circulate, such as the endothelial cells lining the blood vessels, can be transfected with nucleic acid encoding the suppressor factor. The suppressor factor protein would be released into the blood stream where it alters the effect of IL-2 on circulating IL-2R bearing cells. 3) In a similar manner, epithelial cells transfected with a nucleic acid of the invention may secrete suppressor factor protein, altering the effect of IL-2 on proximal IL-2R bearing cells. Epithelial cells, e.g., epithelial cells of the kidney proximal tubule and of the gut, activate or inactivate T-cell proliferation and are thus expected to come into proximity with them. 4) Finally, autoreactive T-cells may themselves be transfected with the nucleic acid of the invention, such that the T-cells make and secrete suppressor factor which would in turn alter the effect of IL-2 on themselves. Cells transfected in the manner of the methods above are expected to equally alter the effect of IL-4 on IL-4R bearing cells.

Cells to be transfected can be accessed in several ways, either by removing the cells from a patient for transfection, or by administering a vector, e.g., a virus, comprising a suppressor factor-encoding nucleic acid to the patient. Alternatively, cells, e.g., cells of a cell line, or of a graft, can be transfected in vitro and then introduced to the patient.

Diagnosis

Human patients suffering from autoimmune diseases will be expected to exhibit abnormally low levels of the suppressor factor of the invention in the blood and in the endocrine portion of the pancreas. Assaying blood, other biological fluid samples, or pancreatic tissue samples for the factor can thus provide a means of monitoring therapy and assessing the immune status of patients with autoimmune diseases, e.g., IDDM. Such assays can be carried out by conventional immunoassay methods employing antibodies to the suppressor factor, made by conventional techniques in which a rabbit is immunized with the factor and the resulting antibody harvested and labeled, e.g., with a radioisotope or a fluorescent tag.

Therapy

For use in therapy, the suppressor factor protein of the invention is first purified to homogeneity using conventional techniques. It is then mixed with a pharmaceutical carrier and administered intravenously or by some other standard method, or used to perfuse a graft to be transplanted. The factor can be used to treat autoimmune diseases such as systemic lupus erythematosus (SLE), type 1 diabetes, and rheumatoid arthritis, as well as other disease states involving the immune system such as graft versus host disease. Dosage will be in the range of dosages used for currently available immunosuppressive agents.

Cells

The anergic T-cell clone IS-2.15 is a recombinant human IL-2 (rIL-2) dependent, non-cytolytic, CD8+, Vβ11+ clone propagated from the islets of 2 month old euglycemic male NOD mice.

The following examples are meant to illustrate the invention and are not meant to limit the invention.

EXAMPLE 1

This example illustrates a method for gene transfer which may be used to administer immunosuppressive proteins to the kidney area and provides a test for the effectiveness of constructs.

Macrophage (Mϕ) colony-stimulating factor (CSF-1) expression precedes renal injury in autoimmune MRL-lpr) mice and is responsible for Mϕ proliferation and survival in glomeruli. [The purpose of this study was to test the capacity of local and systemic expression of Mϕ growth factors, CSF-1 and granulocyte-Mϕ CSF (GM-CSF), to initiate renal injury in normal (C3H-++,MRL-++) and autoimmune prone (C3H-lpr, MRL-lpr), mice.] We designed a gene transfer system to deliver cytokines into the kidney by transducing TEC using retroviral vector (MFG) expressing CSF-1, GM-CSF or interleukin-6(IL-6). Transduced cells (90%) constitutively secreted high levels of stable, bioactive protein. We placed transduced primary tubular epithelial cells (TEC, $5 \times 10^6$ cells) under the left renal capsule of normal and autoimmune prone mice prior to renal injury and evaluated renal pathology 3, 7, 14 and 28 d post-implant.

CSF-1 & GM-CSF, but not IL-6 nor uninfected TEC, caused an influx of cells intrarenally radiating from the implant site by 3–8 d (mostly Mϕ) which was maximal by 15–28 d (mostly T cells) in strains with lpr. Renal injury was most severe in the MRL-lpr strain. By comparison, the kidney of MRL-++ and C3H mice remained normal. Although implanted transduced TEC caused a sustained increase of CSF-1, GM-CSF and IL-6 in the circulation, the contralateral kidney remained unaffected. In conclusion, gene transfer of Mϕ growth factors into the kidney initiates severe local renal injury in autoimmune prone mice with lpr gene but does not compromise the kidney in non-autoimmune hosts. In addition, systemic delivery of growth factors at these concentrations does not induce renal damage. These studies offer a novel gene transfer approach to explore the impact of local and systemic cytokine production on renal injury.

TABLE 4

| Donor (strain) | Recipient (strain) | Intrarenal | | | |
|---|---|---|---|---|---|
| | | CSF-1 | GM-CSF | IL-6 | uninfected |
| C3H-++ | C3H-++ | 0 ± 0 | 0 ± 0 | 0 ± 0 | 0 ± 0 |
| C3H-++ | C3H-1pr | 1.0 ± 0.2 | 1.0 ± 0 | 0 ± 0 | 0 ± 0 |
| MRL-1pr | MRL-++ | 0 ± 0 | 0 ± 0 | 0 ± 0 | 0 ± 0 |
| MRL-1pr | MRL-1pr | 1.6 ± 0.2* | 2.8 ± 0.3* | 0 ± 0 | 0 ± 0 | n = 2–3
28 d after implant
*p < 0.05
Grade: 0 (none)–3 (severe)

EXAMPLE 2

This example illustrates retroviral delivery to the kidney.

We constructed a gene transfer system to deliver cytokines into the kidney and circulation. We selected a recombinant Moloney murine leukemia virus retroviral vector (MFG) system which efficiently transfers cytokine genes without the need of selection. Primary tubular epithelial cells (TEC) derived from normal (C3H/Fej, MRL-++) and autoimmune (C3H-lpr) mouse strains were cultured and transduced with retroviral vectors expressing colony stimulating factor-1 (CSF-1), granulocyte-macrophage CSF (GM-CSF) and interleukin-6 (IL-6). Each cytokine was constitutively released by most cells (90%) as determined by colony forming assays and immunoperoxidase methods. Uniform levels of cytokines were released by TEC from each strain. These TECs remained capable of dividing and secreting stable amounts of biologically active cytokines for >8 mo in culture. We placed transduced TEC ($5 \times 10^6$) under the renal capsule and monitored cytokine secretion. TEC formed nests of cells that were vascularized by extensions from peripheral capillaries. Co-expression of cytokine and the β-galactosidase gene established that TEC remained viable and capable of producing cytokines in the kidney for at least 28 d. These retrovirally infected TEC delivered a continuous supply of CSF-1, GM-CSF or IL-6 into the circulation from 8–28 d.

This example demonstrates a gene transfer system to deliver a continuous supply of cytokines in the kidney and circulation. This system offers a novel, powerful approach for establishing the impact of sustained cytokine expression on renal injury.

TABLE 5

| strain | cytokine | pre-implant (CFU*) | post-implant (CFU*) 8 d | 28 d |
|---|---|---|---|---|
| C3H/Fej | CSF-1 | 0 ± 0 | 1 ± 0 | 12 ± 6 |
| C3H-1pr | CSF-1 | 0 ± 0 | 14 ± 3 | 7 ± 2 |
| MRL-1pr | CSF-1 | 4 ± 0 | 10 ± 3 | 25 ± 5 |
| MRL-1pr | GM-CSF | 0 ± 0 | 13 ± 5 | 15 ± 10 |

*(colony forming units)

EXAMPLE 3

This example illustrates the Allogeneic transplant model which may be used to test the effectiveness of constructs. We have investigated murine islet cell transplants as a model to study allograft rejection (Pankewycz, et al., 1989 *Transplantation*, 47:318; Mackie, et al., 1990 *Transplantation*, 49:1150) and performed allogeneic pancreatic islet cell transplants according to described techniques, herein incorporated by reference (Gotoh, et al., 1985 *Transplantation*, 40:437). Pancreatic islets harvested from DBA/2 ($H-2^d$) mice are transplanted under the renal capsule of 8–10 wk old $B6AF_1$ ($H-2^{b/k, d}$) mice previously rendered diabetic by the beta cell toxin, streptozotocin (250 mg/kg ip). Following successful transplantation, blood glucose returns to normal (<200 mg/dl) within 7 days. Blood glucose levels are assessed every other day throughout the first 50 days post-transplantation, then twice weekly through the next 50 days. Rejection is defined as hyperglycemia in excess of 300 mg/dl or 3 consecutive days of blood glucose >250 mg/dl. This assay may be used to test immunosuppressive constructs for use in both autoimmune and transplant related therapies.

Unmodified graft rejection

Animals are sacrificed at days 4, 8, or 12. Histological examination of day 4 pancreatic islet allografts showed early leukocyte infiltration but well preserved islet morphology. Day 8 allografts showed a massive leukocyte infiltrate with severe islet injury; however, the islets were still discernable. By day 12 the islets were completely destroyed. There was early organization of the cellular exudate, and the leukocyte infiltrate was less intense than observed on day 8. Immunoperoxidase staining of day 12 allograft specimens showed that most infiltrating leukocytes were macrophages, and expressed endogenous peroxidase.

Tolerance induction

Bluestone and his colleagues first reported that high doses of hamster and anti-mouse CD3 mAb caused profound immunosuppression (Hirsch, et al, 1988 *J. Immunol.*, 140:3766). It was noted that lower doses, closer to clinically applied doses, produced tolerance in many, but not all, islet allograft recipients (Mackie, et al., 1990 *Transplantation*, 49:1150). In a new study using the same high total dose employed by Bluestone but administered over a 3 d period, permanent engraftment of 90% of DBA/2 into $B6AF_1$ islet graft recipients was obtained. Daily treatment with a recombinant IL-2 diphtheria toxin related fusion protein ($DAB_{486}$-IL-2) also causes a 50% incidence of graft tolerance (Pankewycz, et al., 1989 *Transplantation*, 47:318). Twice daily therapy results in 90% incidence of tolerance.

EXAMPLE 4

PCR based identification of activation associated transcripts

PCR can be used to identify activation associated transcripts. The PCR technique was adapted for mRNA phenotyping from tissues that were snap frozen in liquid nitrogen in the following fashion: (a) total cellular RNA was isolated using the cesium chloride modification of the guanidine isothiocyanate method, (b) first-strand cDNA was synthesized using oligo (dT) primer and M-MLV reverse transcriptase, and (c) the cDNA was amplified (25 cycles) with sequence specific oligonucleotide primer-pairs and thermostable DNA polymerase (Taq DNA polymerase), using a DNA thermal cycler. Each sample was co-amplified with a β-actin oligonucleotide primer as an internal control. The PCR products were analyzed by agarose gel electrophoresis for the predicted fragment size and for specificity by Southern hybridization using $^{32}P$ randomly primed partial length DNA probes. In each case, the radiolabelled cDNA probes identified a single characteristic band when applied to RNA-revived from ConA+RNA activated splenic sutures. We have determined the number of cycles required for attainment of the linear portion of the radioactivity curve following hybridization with radiolabeled probes. For detection of each of the mRNAs 25 cycles of PCR amplification was adequate for this purpose. The antisense and sense primers hybridize to sequences encoded by different exons (Table 6). This precaution reduces the possibility that DNA, rather than RNA, sequences are unwittingly selected for amplification and confused with RNA based amplification. In each experiment, one control sample lacks reverse transcriptase in order to identify preparations with contaminant DNA. The relative abundance of each amplified product was semiquantitatively evaluated using the PHOSPHOR IMAGER system (Molecular Dynamics, Inc.).

EXAMPLE 5

Correlation of allograft transcriptional activity with histology

RNA was isolated from allografts, lymphoid tissue and non-lymphoid tissue at days 1, 4 (the time of maximal cellular infiltration), 8, 12 (the time of complete graft destruction) and day 19. Peak IL-2 and IFNγ gene transcription in the allograft closely correlated in time with the peak of leukocytic infiltration (FIGS. 1, 2 and Table 7). IL-2 and IFNγ transcripts were expressed on day 8, but not at day 1, and only sporadically at days 4 and 12. Whereas IL-2 transcripts were detected in all rejecting allografts at day 8 post-transplant, IL-4 transcripts, although present in some grafts, were barely detectable at any time point. Granzyme B transcripts were detected in most allografts even as early as day 1 in some grafts. Nonetheless, co-amplification of granzyme B and TCR Cα sequences revealed that the ratio of granzyme B to TCR Cα rose progressively through days 1 to 12 (FIG. 3). The ratios of granzymes B to TCR Cα transcripts were compared to those obtained from a 72 h Con A activated B6AF$_1$ spleen cell culture. β-actin transcripts were detected in all specimens. Table 7 shows the pattern of IL-2, IFNγ, IL-4 and grandzyme B transcription at Day 8 in acutely rejecting mice. It is noteworthy that detection of IL-2 and granzyme B transcripts in the allograft foreshadowed their appearance in the lymph nodes and spleen. However, the data also indicates that the pattern of transcriptional activity in the spleen at day 8 closely reflects the pattern of transcriptions in the allograft.

EXAMPLE 6
Molecular characterization of allograft tolerance

Animals are treated with immunosuppressive regimes (e.g., anti CD3, DAB$_{486}$-IL-2, or IL-2 Fc) to induce permanent engraftment ["tolerance"] and the transcriptional activity is compared with activity in unmodified graft rejection and syngeneic grafts. Animals are sacrificed at sequential time points during the induction and maintenance phase of graft tolerance and mRNA isolated from the graft, spleen and lymph node.

EXAMPLE 7
Transcriptional activity in unmodified, anti-CD3 or DAB$_{486}$-IL-2 treated hosts A reduction in proportion of grafts/spleen bearing detectable IL-2 and IFNγ mRNA was evident in hosts receiving tolerogenic therapies (Table 7). These data suggest that TH1 subset activation is interrupted by tolerogenic therapies. The proportion of tissues bearing detectable granzyme B and IL-4 transcripts was not altered by treatment. Our preliminary results indicate that IL-10 transcription is evident in all grafts from unmodified and treated hosts.

The data and in the preceding two sections indicate that inactivation/destruction of TH1 cells may be closely linked to tolerance induction, and the balance between expression of pro-inflammatory (IL-2, IFNγ) and anti-inflammatory transcripts (IL-10) is markedly altered in hosts receiving tolerogenic therapy.

EXAMPLE 8
Pathology and transcriptional events in pancreatic islet cell allografts during rejection and tolerance induction Using a model of mouse pancreatic islet cell transplantation and the RVT-PCR technique, intragraft and splenic expression of IL-2, IFNγ, IL-2Rα, IL-4, and granzyme B mRNA was studied. An analysis of IL-10 mRNA was initiated. In a totally MHC mismatched transplant (DBA2/J-B6AF1/J), the graft is completely rejected by day 19. Mice were transplanted and sacrificed at 1, 4, 8, 12 and 19 days post transplant. Maximal mononuclear cell infiltration of the allografts occurred at day 8. The peak expression of IL-2 and IFNγ mRNA also occurred at day 8 while meager IL-4 transcripts were detected in some grafts at this point. Peak expression of granzyme B occurred at days 8–12. In a second set of experiments, transplanted mice were treated either with anti-CD3 mAb or an IL-2 toxin fusion protein (DAB/486-IL-2) with doses that we have shown to significantly delay rejection and to induce tolerance in at least 90% of mice. Treated mice were sacrificed 8 days post transplant for RNA extraction. IL-2 and IFNγ transcription was markedly reduced. Preliminary data indicate that tolerogenic therapies do not block IL-10 expression.

EXAMPLE 9
Islet cell graft infiltrating T-cell lines and T-cell clones

Using the methods described by Fitch and Gajewski (Fitch, 1991 *Current Protocols in Immunology.* 3.13.1–3.13.11), both rIL-2 (80 U/ml) and rIFNγ (4000 U/ml) or a mixture of rIL-2 and Con A supernatants to derive outgrowths of islet graft infiltrating T cells were used. The IL-2 and IFNγ mixture favors TH1 cell growth while the latter mixture favors TH2 cell growth (Fitch, 1991 *Current Protocols in Immunology.* 3.13.1–3.13.11). The outgrowths are then cultivated in media that favors the maintenance of TH1 or TH2 cells. Other clones are derived using only rIL-2 and donor strain islets. To date we have derived at least two T-cell lines cultivated under TH1- and one cultivated under TH2-promoting growth media from day 2, 8, 12, 19 unmodified and DAB\486-IL-2 treated hosts. Aliquots of these lines have been frozen and stored. A limiting dilution method (MacDonald, et al., 1990 *Immunol. Rev.* 51:93) to derive T-cell graft infiltrating clones from day 8 unmodified and DAB\486-IL-2 treated hosts was used. The media used to selectively propagate TH1 and TH2 clones does yield a high proportion of CD4+ clones while use of a protocol utilizing IL-2 and islet cell cultures primarily yields CD8+ T-cells.

EXAMPLE 10
Suppressive effects of IS-2.15 T-cells

Transfer of IS-2.15 T-cells into prediabetic NODs prevents rapid induction of diabetes of accelerated diabetogenic autoimmunity (Pankewycz, O., et al., 1991, *Eur. J. Immunol.*, 21:873). The suppressive effects of IS-2.15 are characterized in the following detailed description.

H-4, G-3, #3 and #5 cells are CD3+, CD8+islet-infiltrating T-cell clones isolated from the islets of 2 month old euglycemic NOD mice as previously described (Pankewycz, O., et al., 1991, *Eur. J. Immunol.*, 21:873). HT-2 (Watson, J., 1979, *J. Exp. Med.*, 150:151) and CTLL-2 (Gillis, S., et al., 1977, *Nature,* 268:154.) murine IL-2/IL-4 dependent T-cells were obtained from Dr. D. Perkins (Brigham and Women's Hospital, Boston, Mass.) and the American Type Culture Collection (Rockville, Md.), respectively.

T-cells were cultured in RPMI-1640 media (Gibco, Grand Island, N.Y.) supplemented with 10% (vol/vol) fetal bovine serum, 100 g/ml streptomycin, 100 u/ml penicillin, 10 μM HEPES, 1 μm sodium pyruvate, $10^{-5}$ M 2-mercaptoethanol and 1% minimal essential amino acids (complete RPMI medium). In some cultures irradiated (3,000 rads) syngeneic splenic cells were plated with IS-2.15, G-3 and H-4 cloned T-cells. T-cell growth factor (TCGF) was added to some HT-2 and CTLL-2 cell cultures.

Supernatant from NOD T-cell clones

T-cell clones were isolated from feeder cells by Lympholyte M (Cedarlane Lab. Hornby, Ontario, Ca.) gradient separation and placed in culture at a concentration of $10^6$ cells/ml in complete RPMI medium for 24 hours. After this period, T-cells were pelleted by centrifugation, and the supernatant was aliquoted in siliconized tubes and stored at −70° C.

Proliferative responses against immobilized mitogenic mAbs

Fifty×$10^3$ cloned T-cells were cultured in round bottom 96-well plates in 0.2 ml of complete RPMI medium alone or with 5×$10^5$ irradiated (3,000 rads) syngeneic spleen cells and different concentrations of immobilized anti-CD3 or anti-Vβ11 mAbs. Wells were coated with mAbs for 2 hours at 37° C. Cells were cultured in the mAb coated plates for 48 hours, pulsed with 1 μCi [$^3$H]thymidine during the last 6 hours of culture, harvested with a semiautomated cell harvester (PHD, Cambridge, Mass.), and cellular [$^3$H] thymidine incorporation was measured by liquid scintillation counting.

Proliferative responses against syngeneic pancreatic islets

Islets of Langherhans from NOD mice were obtained as previously described (Pankewycz, O., et al., 1991, *Eur. J.*

*Immunol.*, 21:873), irradiated (3,000 rads) and placed in flat-bottom 96-well plates with $10^5$ T-cells in complete RPMI. Cells were cultured for 6 days, pulsed with 1 μCi [$^3$H]thymidine during the last 6 hours of culture, harvested with a semiautomated cell harvester (PHD, Cambridge, Mass.), and cellular incorporation of [$^3$H]thymidine was measured by liquid scintillation counting.

Detection of suppressor activity

HT-2 or CTLL-2 cells were cultured at a concentration of $10^5$ cells/well in a final volume of 0.2 ml complete RPMI media±rIL-2±supernatants of NOD T-cell clones and ±anti-TGF-β1 or anti-TGF-β2 mAbs. After 20 hours of culture, each well was pulsed with 1 μCi [$^3$H]thymidine, incubated for an additional 4 hr, and harvested with a semiautomated cell harvester (PHD, Cambridge, Mass.). Tritiated thymidine incorporation was measured by liquid scintillation counting. Suppressor activity was calculated according to the following formula: % suppressor activity: [experimental samples (supernatant+IL-2)−negative control] (no IL-2)/[positive control (IL-2 alone)−negative control]. Results were given as the mean of triplicate cultures. SEM did not exceed 12.5% of means. Similar results were found for HT-2 or CTLL-2 cells.

Bioassay for Transforming Growth Factor β (TGF-β)

Mink lung epithelial (CCL-64) TGF-β indicator cells were used as previously described (Danielpour, D., et al., 1989, *J. Cell. Physiol.*, 138:79). Briefly, $10^5$ cells/ml were placed in 24 well plates with culture media containing T-cell supernatants and cultured for 22 hours. The cells were then pulsed with 0.5 μCi/well of [$^3$H]thymidine for 2 hours, and [$^3$H]thymidine incorporation was measured by liquid scintillation counting. A TGF-β standard curve was constructed using TGF-β indicator cells cultured with serial dilutions of a known amount of TGF-β.

Flow cytometric analysis

HT-2 cells (2.5×$10^5$) were suspended in 50 μl Hank's balanced salt solution containing 0.1% sodium azide and 20% (vol/vol) horse serum. The cells were incubated for 30 minutes at 4° C. with 0.2 μg of anti-IL-2Rα mAb, washed and incubated with anti-rat IgG-FITC conjugated 30 minutes at 4° C. Subsequently, the cells were washed, resuspended in 2% paraformaldehyde and analyzed using a Becton and Dickinson FACS analyzer.

EXAMPLE 11

Partial size purification

Supernatants harvested from 24 hour cultures of IS-2.15 T-cells grown in complete RPMI without fetal bovine serum were loaded into 10, 30 and 100 KD membrane Centricon microconcentrator tubes (Amicon, Danvers, Mass.) with different membrane size cut-offs (10, 30 and 100 KD) and centrifuged at 6,000 RPM for 60 minutes at 25° C. The concentrates and filtrates were tested for biological activity as described previously.

EXAMPLE 12

RNA extraction and Polymerase-Chain reaction (PCR) procedure

Cytoplasmic RNA was extracted from T-cell clones by the NP-40 lysis method. Two micrograms of RNA were reverse transcribed into cDNA using random hexamer oligo(dN)$_6$ as primer (BRL) and AMV reverse transcriptase (Promega, Madison, Wis.) in a 50 μl reaction. Ten microliters of the cDNA was amplified by PCR. PCR conditions implemented in a 50 μl reaction were as follows: 75–750 pmol of each primer (see below), 200 μM each dGTP, dATP, dCTP and dTTP (Perkin-Elmer/Cetus, Emeryville, Calif.), 50 mM KCl, 10 mM Tris-HCl, pH 8.3, 1.5 mM MgCl$_2$, and 2 units Taq DNA polymerase ("AmpliTaq", Perkin-Elmer/Cetus, Emeryville, Calif.). The following primers were used: IL-2 sense primer 5'-TGATGGACCTACAGGAGCTCCTGAG-3' (nucleotides 203'–227') (SEQ ID NO: 1); IL-2 antisense primer 5'-GAGTCAAATCCAGAAACATGCCGCAG-3' (nucleotides 370'–346') (SEQ ID NO: 2); IL-4 sense primer 5'-CGAAGAACACCACAGAGAGTGAGCT-3' (nucleotides 231–255) (SEQ ID NO: 3); IL-4 antisense primer 5'-GACTCATTCATGGTGCAGCTTATCG-3' (nucleotides 411'–387') (SEQ ID NO: 4); IL-6 sense primer 5'-TGGAGTCACAGAAGGAGTGGCTAAG-3' (nucleotides 581'–605') (SEQ ID NO: 5); IL-6 antisense primer 5'-TCTGACCACAGTGAGGAATGTCCAC-3' (nucleotides 735'–711') (SEQ ID NO: 6); IFN-γ sense primer 5'-AGCGGCTGACTGAACTGAACTCAGATTGTAG-3' (nucleotides 841'–865') (SEQ ID NO: 7); IFN-γ antisense primer 5'-GTCACAGTTTTCAGCTGTATAGGG-3' (nucleotides 1084'–1061') (SEQ ID NO: 8); TNF-α sense primer 5'-GGCAGGTCTACTTTGGAGTCATTG-3' (nucleotides 820'–843') (SEQ ID NO: 9); TNF-α antisense primer 5'-ACATTCGAGGCTCCAGTGAATTCCAG-3' (nucleotides 1127'–1102') (SEQ ID NO: 10); TGF-β sense primer 5'-AAGTGGATCCACGAGCCCAA-3' (nucleotides 1277'–1298') (SEQ ID NO: 11); TGF-β antisense primer 5'-CTGCACTTGCAGGAGCGCAC-3' (nucleotides 1521'–1502') (SEQ ID NO: 12), as previously described (Murray, L. J., et al., 1990, *Eur. J. Immunol.* 20:163). Reactions were incubated in a Perkin-Elmer/Cetus DNA thermal cycler for 45 cycles (denaturation 30 seconds, 95° C.; annealing 30 seconds, 56° C.; extension 60 seconds, 72° C.). Fifteen microliters of the reaction product was electrophoresed through a 1.2% agarose gel and transferred onto a nylon membrane by capillary action (Zeta-probe, BioRad, Richmond, Calif.). Blots were hybridized at 65° C. for 18 hours with 1 mM EDTA, 0.5 M NaH$_2$PO$_4$ (pH 7.2) and 7% sodium dodecyl sulfate (SDS), and radiolabeled with probes for murine rIL-2 (90 bp probe inserted in pBS) (Kasima, N., et al., 1985, *Nature*, 313:401), IL-4 (1 kb probe inserted in pXM) (Lee, F., et al., 1986, *PNAS*, 83:2063), IL-6 (1 kb probe inserted in pXM) (Chiu, C. P., et al., 1988, *PNAS*, 85:7099), IFN-γ (643 bp probe inserted in pmsl0) (Gray, P. W., et al., 1983, *PNAS*, 80:5842), TNF-α (480 bp probe inserted in p-mTNF-1) (Fransen, L. et al., 1985, *Nucl. Ac. Res.*, 13:4417) and human TGF-β (2.14 kb probe inserted in pBR327) (Derynck, R., et al., 1986, *J. Biol. Chem.*, 261:4377). After hybridization the blots were washed twice at 65° C. with 1 mM EDTA, 40 mM NaH$_2$PO$_4$ (pH 7.2) and 5% SDS for 30 minutes, and twice with 1 mM EDTA, 40 mM NaH$_2$PO$_4$ (pH 7.2) and 1% SDS for 30 minutes at 65° C. Blots were then exposed to Kodak X-AR film at −70° C. for 6–24 hours. Results of the analysis of cytokine gene expression are described below.

EXAMPLE 13

T-cell receptor (TCR) crosslinking did not induce proliferation in an IS-2.15 clone To determine whether IS-2.15 is an anergic or normally responsive T-cell clone, culture plates were coated with mitogenic anti-TCR/CD3 complex and cellular proliferation was measured. Unlike NOD spleen cells, IS-2.15 T-cells did not proliferate in response to anti-CD3 or anti-Vβ11 mAbs (FIG. 5). Increasing the concentration of either the mAbs (FIG. 5A and FIG. 5B) or the concentration of responder cells (FIG. 5C) failed to produce mitogenesis. These findings have been corroborated in each of three subsequent experiments. To determine whether this unresponsiveness to anti-TCR/CD3 mAbs was merely caused by a delay in proliferation the culture period was prolonged to 5 days. A failure to proliferate in response to anti-CD3 or anti-Vβ11 mAbs was also noted at 5 days.

EXAMPLE 14

IS-2.15 clone proliferates, albeit slowly, to syngeneic spleen cells or pancreatic islets To assess whether IS-2.15 T-cells are autoreactive $5 \times 10^5$ IS-2.15 T-cells/ml were co-cultured with 50–70 irradiated syngeneic NOD islets/ml or $10^6$ spleen cells/ml in a final volume of 200 Al. Although IS-2.15 T-cells responded with a far lower proliferative rate than many other organ-specific islet infiltrating T-cell clones (Pankewycz, O., et al., 1991, *Eur. J. Immunol.*, 21:873), IS-2.15 T-cells do proliferate, albeit weakly, in response to islets. Table 3 shows a representative, i.e. one of three, experiment.

EXAMPLE 15

IS-2.15 supernatant specifically inhibits rIL-2 dependent Proliferation in rIL-2 dependent murine T-cell lines To investigate the possibility that IS-2.15 T-cells produce an immunosuppressive factor, the ability of IS-2.15 to block IL-2 stimulated proliferation of murine T-cells was tested. Two different murine IL-2 dependent T-cell lines, CTLL-2 and HT-2, were used as defined model systems for this analysis. When either of these T-cell lines are pre-incubated with IS-2.15 supernatant, their proliferative response to RIL-2 was abrogated, indicating that a suppressor or anti-proliferative substance is present in this supernatant (FIG. 6A). To examine whether this inhibitory substance was produced by other islet infiltrating NOD T-cell clones, supernatants from two additional islet-infiltrating clones were analyzed. Neither clone produced a substance that inhibited the proliferative response of CTLL-2 or HT-2 cells to rIL-2. Supernatants from cloned G-3 cells did not modify rIL-2 stimulated proliferation, whereas supernatants from cloned H-4 cells actually amplified rIL-2 dependent T-cell proliferation. Titration of IS-2.15 suppressor activity showed that supernatant dilutions of 1/16 were suppressive (FIG. 6B).

Although IL-2 indicator cells (CTLL-2 AND HT-2) cultured with IS-2.15 supernatant and rIL-2 do not proliferate, HT-2 cells remain viable after interaction with the supernatant as determined by a trypan blue exclusion assay. Viability of cells cultured for 24 hours with rIL-2 was 99% with or without addition of IS-2.15 supernatant.

EXAMPLE 16

IS-2.15 supernatant inhibitory activity is not due to TGF-β. Since TGF-β is the only cytokine known to directly block the response of T-cells to IL-2, the capacity of neutralizing anti-TGF-β1 and anti-TGF-β2 antibodies to restore proliferation of HT-2 cells cultivated with rIL-2 and IS-2.15 T-cell supernatants was tested. Anti-TGF-β1 and anti-TGF-β2 antibodies, used at neutralizing concentrations as described elsewhere (Danielpour, D., et al., 1989, *J. Cell. Physiol.*, 138:79), failed to restore rIL-2 dependent proliferation of HT-2 cells. Moreover, TGF-β bioactivity was not detected in IS-2.15 T-cell supernatants using TGF-β dependent epithelial lines as indicator cells. It is doubtful that the active moiety is TGF-β.

EXAMPLE 17

Inhibition of rIL-2 stimulated proliferation of HT-2 cells is not readily reversible and is not due to downregulation of the IL-2 receptor (IL-2Rα)

Saturating concentrations of rIL-2 do not restore IL-2 dependent proliferation of HT-2 cells cultured with IS-2.15 supernatant (FIG. 5A). The mechanism of this inhibitory activity was investigated. HT-2 cells were cultured with rIL-2 (50 u/ml)±IS-2.15 supernatant (10%, vol/vol) for 24 hours. HT-2 cells were washed twice and recultured for an additional 24 hours with different concentrations of rIL-2. HT-2 cells that were not pretreated with IS-2.15 supernatant responded to rIL-2. In contrast, HT-2 cells pre-cultured for 24 hours with IS-2.15 supernatant and washed did not proliferate in response to rIL-2. Since cell viability was not compromised by IS-2.15 supernatant (99% in the two groups), a cytotoxic effect is not responsible for the anti-proliferative activity (FIG. 7).

Figure 8B:
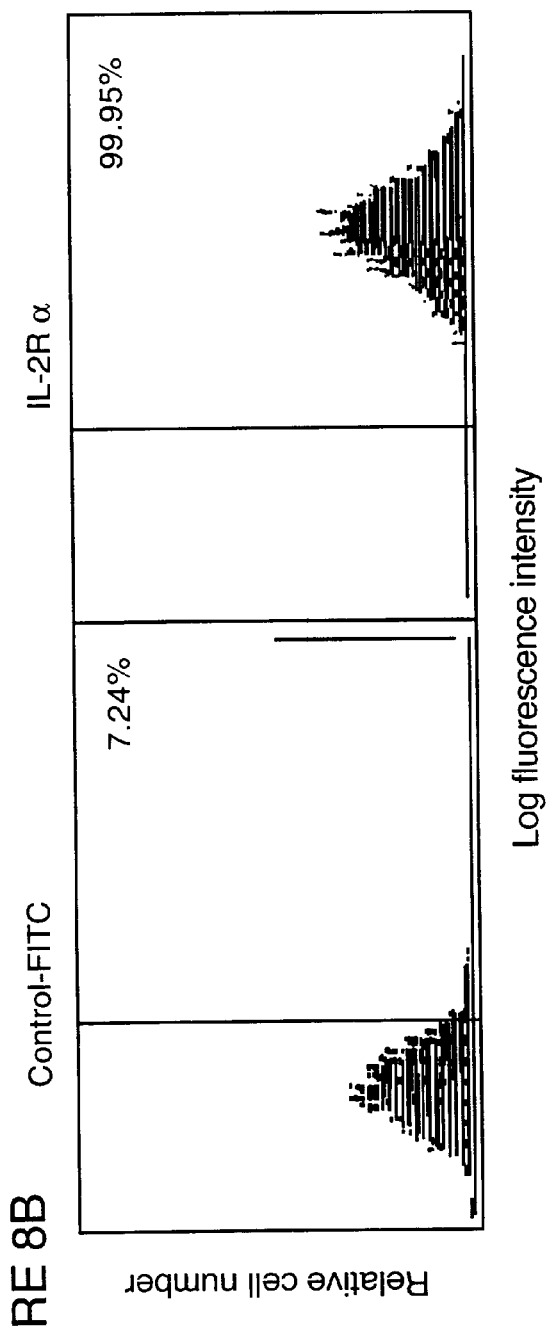

In theory, downregulation of IL-2Rα expression could account for these effects. Therefore, IL-2Rα expression was examined by flow cytometry after culturing HT-2 cells with rIL-2 (50 u/ml)±IS-2.15 supernatant (10%, vol/vol). IS-2.15 supernatant did not inhibit IL-2Rα expression in HT-2 cells (FIG. 8).

EXAMPLE 18

IS-2.15 supernatant inhibitory factor is a heat-sensitive protein with a molecular weight between 10 and 30 KD The inhibitory activity of IS-2.15 upon IL-2 dependent proliferation was completely destroyed by pre-heating IS-2.15 supernatant for 15 minutes at 65° C. Size selective ultracentrifugation procedures indicate that the molecular weight of this substance is between 10 and 30 KD (FIG. 9).

EXAMPLE 19

Analysis of cytokine gene expression by PCR

Messenger RNA was extracted from each of the 3 islet-infiltrating NOD T-cell clones (IS-2.15,H-4,G-3) and amplified via PCR, as described above. TGF-β encoding mRNA was detected only in the IS-2.15 clone. This clone also expresses TNF-α mRNA. None of the clones expressed IL-2 encoding mRNA; IL-4 encoding mRNA was detected only in the H-4 islet-infiltrating T-cell clone. This finding correlated with the ability of the H-4 clone supernatant to increase proliferation of the IL-4 and IL-2 sensitive HT-2 line to rIL-2 (FIG. 6A). In contrast, the G-3 clone did not express IL-2 or IL-4 encoding mRNA. All 3 clones expressed IL-6 and IFN-γ mRNA.

EXAMPLE 20

Purification of the IL-2.15 suppressor factor protein

The IS-2.15 suppressor factor protein or its component polypeptide(s) can be purified using conventional methods of protein purification known to one schooled in the art, e.g., methods including but not limited to precipitation, chromatography, immunoadsorption, or affinity techniques. The polypeptide can be purified from starting material using the IS-2.15 supernatant, an IS-2.15 suppressor factor cDNA or genomic DNA, as described below, or using a recombinant form of either of these DNAs genetically engineered into an overproducing cell line.

EXAMPLE 21

Isolation of a human IL-2.15 suppressor factor cDNA and genomic DNA

A cDNA encoding the IL-2.15 suppressor factor can be isolated from a human expression library by screening with antibodies to the suppressor factor. Antibodies for screening can be raised in an animal, for example a rabbit. Possible immunogens include but are not limited to 1) a purified fragment of the suppressor factor protein obtained by conventional methods of protein separation as described above, or 2) a partially purified sample of IL-2.15 suppressor factor. The protein sample can be partially purified by fractionating an IL-2.15 supernatant by size, as described above. Antibodies are labeled with a suitable label and are then used as probes to screen an expression library. The cDNA library can be generated by isolating poly(A$^+$) mRNA from the IL-2.15 cell line, converting the RNA to double stranded cDNA (Aruffo, A., et al., 1987, *PNAS,* 84:8573–7) and ligating the cDNA into a λ expression vector, for example λgt11 (Clontech), or into the expression vector pCDNA-1 (Invitrogen, San Diego). Positive clones can be confirmed by testing for the ability to block IL-2 stimulated T-cell proliferation.

The human suppressor factor gene can be cloned by analogous methods, for example by using a human cDNA library. The IL-2.15 cDNA sequences identified above can be used as oligonucleotide probes to obtain the analogous human suppressor factor cDNA or genomic DNA by methods known to those skilled in the art.

What is claimed is:

1. A method of inhibiting the rejection of an islet cell transplanted into a human patient, the method comprising:

(a) introducing into an islet cell, ex vivo, a nucleic acid sequence encoding CTLA4-Ig operably linked to a promotor, wherein the CTLA4-Ig is expressed by the islet cell, and (b) transplanting the islet cell into the patient, wherein CTLA4-Ig is expressed at al level sufficient to inhibit the rejection of the transplanted cell.

* * * * *